(12) United States Patent
Demain et al.

(10) Patent No.: US 6,383,773 B2
(45) Date of Patent: *May 7, 2002

(54) PENICILLIN CONVERSION

(75) Inventors: Arnold L. Demain, Wellesley, MA (US); Hiroshi Cho, Tokyo (JP); Jacqueline M. Piret, Cambridge, MA (US); Josè L. Adrio, Leon; Maria-Josefa E. Fernandez, Madrid, both of (ES); Marco A. Bàez-Vàsquez, Monterrey (MX); Gilberto Hintermann, Cambridge, MA (US)

(73) Assignee: Massachusetts Institute of Technology, Cambridge, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/296,903

(22) Filed: Apr. 22, 1999

Related U.S. Application Data

(60) Provisional application No. 60/082,800, filed on Apr. 23, 1998.

(51) Int. Cl.$^7$ .......................... C12P 35/00; C12P 35/08; C12P 35/06
(52) U.S. Cl. .............................. 435/47; 435/48; 435/49
(58) Field of Search .............................. 435/47, 48, 49, 435/50, 51

(56) References Cited

U.S. PATENT DOCUMENTS

| | | | |
|---|---|---|---|
| 3,941,658 A | | 3/1976 | Laméris et al. |
| 3,966,738 A | | 6/1976 | Verwey et al. |
| 3,996,738 A | | 12/1976 | Justus |
| 4,003,894 A | | 1/1977 | Verweij et al. |
| 4,007,202 A | | 2/1977 | Verweij et al. |
| 4,035,352 A | | 7/1977 | Verweij et al. |
| 4,046,761 A | | 9/1977 | Verweij et al. |
| 4,108,837 A | * | 8/1978 | Johnson et al. ............. 528/126 |
| 4,178,210 A | | 12/1979 | Demain et al. |
| 4,223,894 A | | 9/1980 | Fabricant |
| 4,307,192 A | | 12/1981 | Demain et al. |
| 5,082,772 A | * | 1/1992 | Dotzlaf et al. ................. 435/49 |
| 5,164,494 A | | 11/1992 | Witkamp et al. |
| 5,318,896 A | | 6/1994 | Conder et al. |
| 5,629,171 A | | 5/1997 | Conder et al. |
| 5,726,032 A | | 3/1998 | Bovenberg et al. |
| 5,731,165 A | | 3/1998 | Bovenberg et al. |
| 5,919,680 A | * | 7/1999 | Sutherland et al. ......... 435/183 |
| 6,020,151 A | * | 2/2000 | Bovenberg et al. ............ 435/47 |

FOREIGN PATENT DOCUMENTS

| | | |
|---|---|---|
| EP | 0268343 | 5/1988 |
| EP | 0532341 | 3/1993 |
| WO | WO 96/38580 | 12/1996 |
| WO | WO 97/20053 | 6/1997 |

OTHER PUBLICATIONS

Baldwin et al., "The enzymatic expansion of penicillins to cephalosporins: side chain specificity", Tetrahedron 43(13): 3009–14 (1987).*

Roy et al., "Characterization of Streptomyces sp. strain DRS–1 and its ampicillin transformation product", Folia Microbiol. 42(4) : 333–6 (1997).*

Svec et al., "Engineering aspects of carriers for immobilized biocatalysts", Biotechnology and Genetic Engineering Reviews 13 : 217–35 (1996).*

Baldwin et al., "Enzymatic Ring Expansion of Penicillins to Cephalosporins: Side Chain Specificity" *J. Chem. Soc. Chem. Commun.* 1466:374–375, 1987.

Baldwin et al., "Genetic Engineering of Cephalosporin Biosynthesis" Abstract P–262 in Program and Adstracts of 7th International Symposium on Genetics of Industrial Microorganisms, Montreal, p. 184, Jun. 26–Jul. 1, 1994.

Bowers et al., "Enzymatic Synthesis of the Penicillin and Cephalosporin Nuclei from an Acyclic Peptide Containing Carboxymethylcysteine" *Biochem. Biophys. Res. Commun.* 120(2):607–613, Apr. 30, 1984.

Cortés et al., "Regulation of the biosynthesis of cephamycin C by *Streptomyces lactamdurans*" *Biochem. Soc. Trans.* 12:863–864, 1972.

Crawford et al., "Production of Cephalosporin Intermediates by Feeding Adipic Acid to Recombinant *Penicillium chrysogenum* Strains Expressing Ring Expansion Activity" *Bio/Tech.*, 13:58–62, Jan. 13, 1995.

Demain, "Production of Beta–Lactum Antibiotics and its Regulation" *Proc. Natl. Sci. Council, ROC, Part B: Life Sciences*, 15(4):251–265, 1991.

Demain, "Biosynthesis of β–Lactam Antibiotics" In *Antibiotics Containing Beta–Lactam Structure* (Demian and Solomon, eds.), Springer–Verlag, Berlin, 189–228, 1983.

(List continued on next page.)

*Primary Examiner*—Sandra E. Saucier
(74) *Attorney, Agent, or Firm*—Choate, Hall & Stewart; Brenda Herschbach Jarrell

(57) ABSTRACT

The present invention provides a biological system for expanding the dethiazolidine ring of penicillins into the dehydrothiazine ring of cephalosporins or cephalosporin precursors. In particular, the invention defines reaction conditions under which expandase enzyme can convert penicillin substrates other than penicillin N into cephalosporins. The invention therefore provides a relatively inexpensive, uncomplicated, and environmentally friendly biological system for cephalosporin production from penicillins, which system can replace the synthetic chemical approaches currently utilized. In particular, the invention provides a system for producing DOAG and/or DAG, which can be enzymatically converted into 7-ADCA and 7-ADAC, which, in turn, can be enzymatically or chemically converted into valuable cephalosporins of commerce.

21 Claims, 30 Drawing Sheets

OTHER PUBLICATIONS

Dotzlaf et al., "Purification and Properties of Deacetoxycephalosporin C Synthase from Recombinant *Escherichia coli* and Its Comparison with the Native Enzyme Purified from *Streptomyces clavuligerus*" *J. Biol. Chem.* 264(17):10219–10227, Jun. 15, 1989.

Dotzlaf et al., "Copurification and Characterization of Deacetoxycephalosporin C Synthase/Hydroxylase from *Cephalosporium acremonium*" *J. Bacteriol.*, 164(4):1611–1618, Apr., 1987.

Dürckheimer et al., "Recent Developments in the Field of Cephem Antibiotics" *Adv. Drug Res.* 17:61–234, 1988.

Jensen et al., "Analysis of Penicillin N Ring Expansion Activity from *Streptomyces clavuligerus* by Ion–Pair High–Pressure Liquid Chromatography" *Antimicrobial. Agents Chemo.* 24(3):307–312, Sep. 1983.

Jensen et al., "Beta Lactams" *Genetics and Biochem. of Antibio. Prod.*, 239–268, 1995.

Jensen et al., "Cephalosporin Formation by Cell–Free Extracts from *Streptomyces clavuligerus*" *J. Antibiot.* 35(10):1351–1360, 1982.

Kirrstetter et al., "Development of new β–lactam antibiotics derived from natural and synthetic sources" *Die Pharmazie* 44:178–184, Mar., 1989.

Kohsaka et al., "Conversion of Penicillin N to Cephalosporin(s) By Cell–Free Extracts of *Cephalosporium acremonium*" *Biochem. Biophys. Res. Commun.* 70(2):465–473, 1976.

Kovacevic et al., "Cloning, Characterization, and Expression in *Escherichia coli* of the *Streptomyces clavuligerus* Gene Encoding Deacetoxycephalosporin C Synthetase" *J. Bacteriol.* 171(2):754–760, 1989.

Kupka et al., "Partial purification and properties of the α–ketoglutarate–linked ring–expansion enzyme of β–lactam biosynthesis of *Cephalosporium acremonium*" *FEMS Microbiol. Lett.* 16:1–6, 1983.

Maeda et al., "The substrate specificity of deaetoxycephalosporin C synthase ("expandase") of *Streptomyces clavuligerus* is extremely narrow" *Enzyme and Microb. Tech.* 17:231–234, 1995.

Mahro et al., "In vivo conversion of penicillin N into a cephalosporin type antibiotic by a non–producing mutant of *Streptomyces clavuligerus*" *Appl. Microbiol. Biotech.* 27:272–275, 1987.

Martin et al., "β–Lactams" In *Fungal Biotechnology* (Anke, ed.), Chapman & Hall, Weinheim, 91–127, 1997.

Shen et al., "Desacetoxycephalosporin C synthetase: importance of order of cofactor/reactant addition" *Enzyme Microb. Technol.* 6:402–404, 1984.

Shibata et al., "Adipoyl–6–Aminopenicillinic Acid is a Substitute for Deacetoxycephalosporin C Synthase (DAOCS)" *Bioorg. & Med. Chem. Lett.* 6(13):1579–1584, 1996.

Stapley et al., "Cephamycins, a New Family of β–Lactam Antibiotics" *Antimicrob. Ag. Chemother.* 2(3):122–131, 1972.

Yeh et al., "Biochemical characterization and evolutionary implication of β–lactam expandase/hydroxylase, expandase, and hydroxylase." In *50 Years of Penicillin: History and Trends* (Kleinhauf and von Doehren, eds.), Public, Prague, 208–223, 1994.

Yoshida et al., "Cell–free ring expansion of penicillin N to deacetoxycephalosporin by *Cephalosporium acremonium* CW–19 and its mutants" *Proc. Natl. Acad. Sci. USA* 75(12):6253–6257, Dec. 1978.

* cited by examiner

FIG. 1B
| NAME | R₁ STRUCTURE |
|---|---|
| PENICILLIN G | 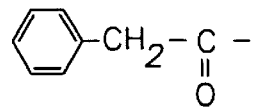 |
| PENICILLIN V | 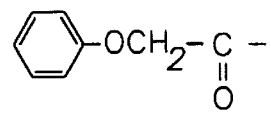 |
| PENICILLIN F | 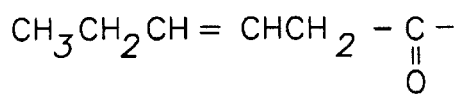 |
| PENICILLIN X | 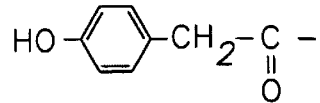 |
| PENICILLIN mX | 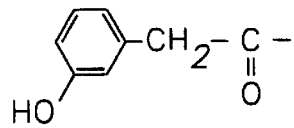 |
| AMPICILLIN | 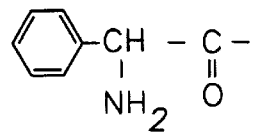 |
| ADIPYL 6APA | 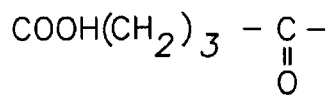 |
| BUTYRYL 6APA | 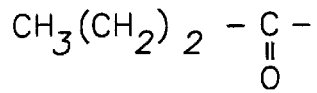 |
*TO FIG. 1B-1*

FROM FIG.1B
FIG.1B-1
| NAME | $R_1$ STRUCTURE |
|---|---|
| VALERYL 6APA | 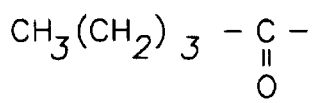 |
| HEXANOYL 6APA | 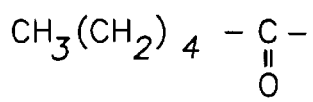 |
| HEPTANOYL 6APA | 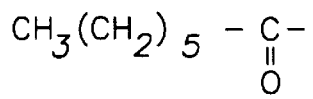 |
| OCTANOYL 6APA | 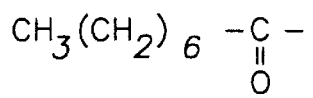 |
| NONANOYL 6APA | 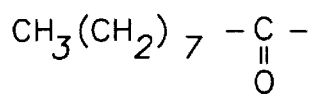 |
| DECANOYL 6APA | 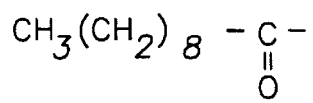 |
| 2-THIOPHENEACETYL 6APA | 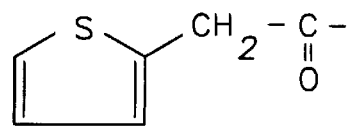 |
| AMOXICILLIN | 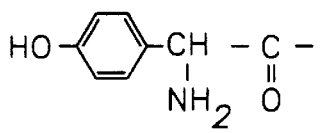 |

FIG.2B
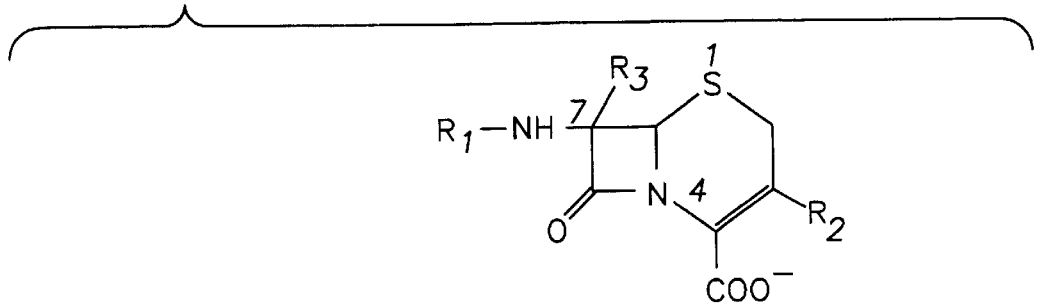
CEPHEM NUCLEUS
| COMPOUND (TRADE NAMES) | $R_1$ | $R_2$ |
|---|---|---|
FIRST GENERATION
CEPHALOTHIN (KEFLIN)
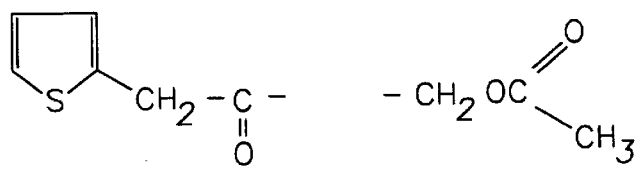
CEFAZOLIN (ANCEF, KEFZOL, others)
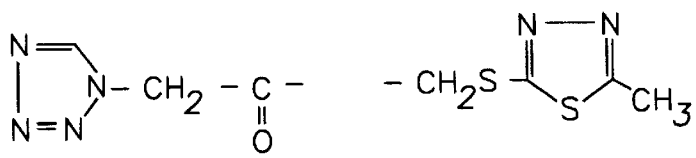
CEPHALEXIN (KEFLET, KEFLEX)
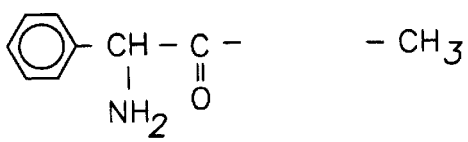  $-CH_3$
CEFADROXIL (DURICEF, ULTRACEF)
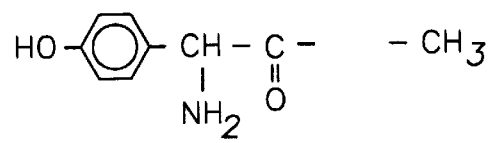  $-CH_3$
TO FIG.2B-1

FIG.2B-1 *FROM FIG.2B*
SECOND GENERATION
| | | |
|---|---|---|
| CEFAMANDOLE (MANDOL) | 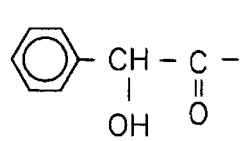 | 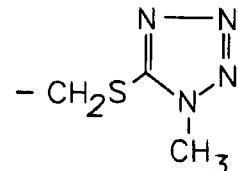 |
| CEFOXITIN† (MEFOXIN) | 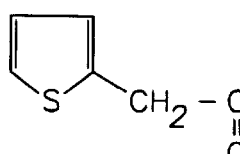 | 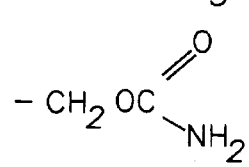 |
| CEFACLOR (CECLOR) | 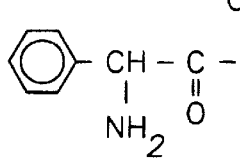 |  −Cl |
| CEFUROXIME (KEFUROX, ZINACEF) CEFUROXIME AXETIL ‡ (CEFTIN) | 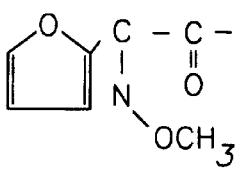 | 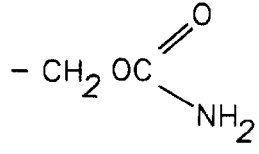 |
| LORACARBEF†+ (CEFZIL) | 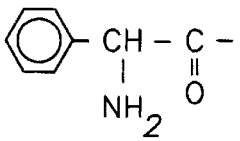 |  −Cl |
| CEFONICID (MONOCID) | 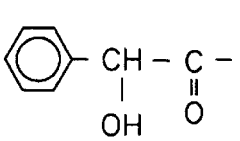 | 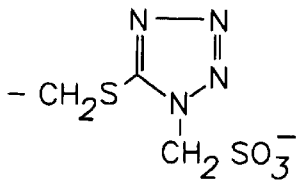 |
| CEFOTETAN (CEFOTAN) | 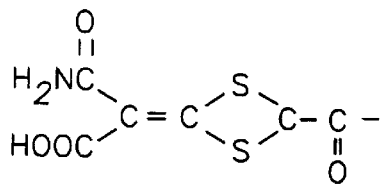 | 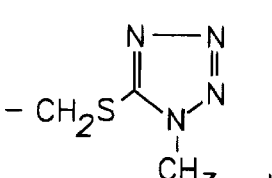 |
*TO FIG.2B-2*

FIG.2B-2   FROM FIG.2B-1
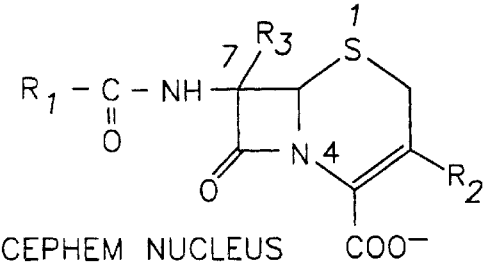
CEPHEM NUCLEUS
|  | $R_1$ | $R_2$ |
|---|---|---|
| CEFORANIDE | 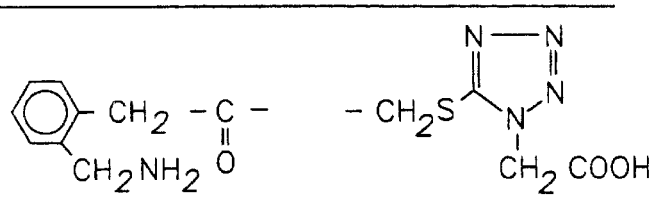 |  |
THIRD GENERATION
| | $R_1$ | $R_2$ |
|---|---|---|
| CEFOTAXIME | 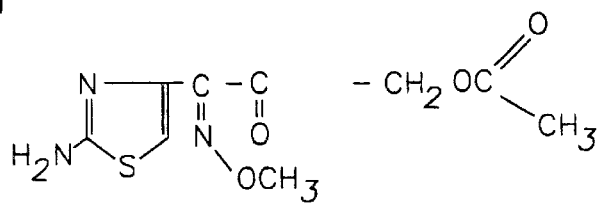 | |
| CEFPODOXIME PROXETIL | 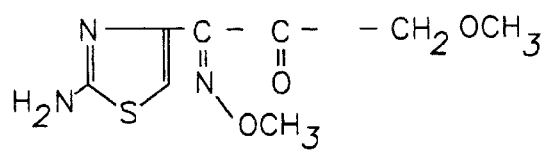 | |
| CEFRIZOXIME | 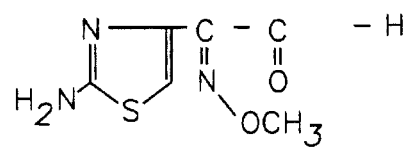 | $-H$ |
| CEFNAXONE | 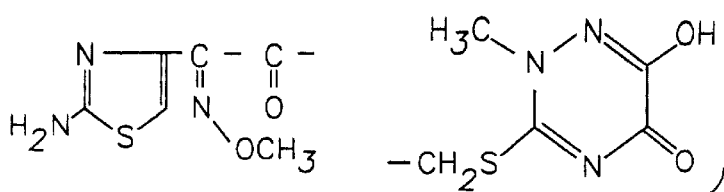 | |
TO FIG.2B-3

FROM FIG.2B-2

CEFOPERAZONE

CEFRADIZIME

---

FOURTH GENERATION

CEFEPIME

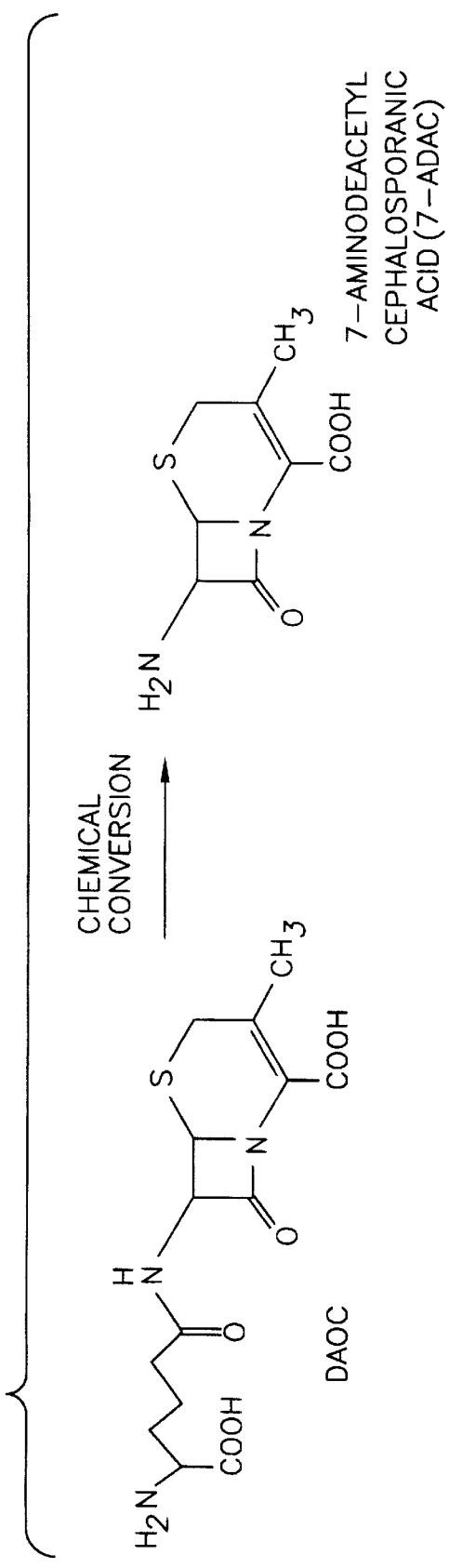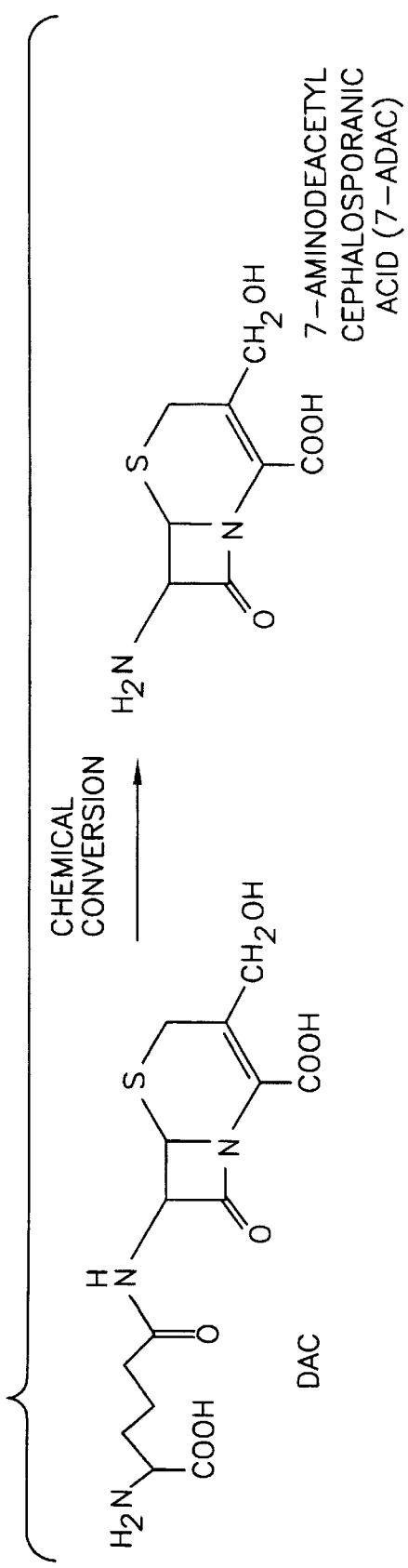
FIG. 4A
FIG. 4B

| | | | |
|---|---|---|---|
| N.lact | 757 | GACAAGCGGGTGGGCAGCAGCCGCACCTCCAGCGTGTTCTTCCTG | 801 |
| S.clav | 751 | GACCAGATAGCGGGCAGCAGCCGCACCTCCAGTGTGTTCTTCCTC | 795 |
| pJAR3-8 | 757 | GACAAGCGGGTGGGCAGCAGCCGCACCTCCAGTGTGTTCTTCCTC | 801 |

| | | | |
|---|---|---|---|
| N.lact | 861 | CAGCATCCCGGCCGAGACCGCCACCTTCGACGACTG | 896 |
| S.clav | 855 | CAGCCTGGACGGCGAGACCGCCACGTTCCAGGATTG | 890 |
| pJAR4-5 | 861 | CAGCATCCCGGCCGAGACCGCCACGTTCCAGGATTG | 896 |

(B)

| | | | |
|---|---|---|---|
| N.lact | 446 | CGGCATGGACGCCTTCCTCGACTGCGAACCCCTGCTG | 483 |
| S.clav | 440 | CGGGGTCGAGGCCTTCCTCGACTGCGAGCCGCTGCTG | 477 |
| pJAR2 | 446 | CGGCATGGACGCCTTCCTCGACTGCGAGCCGCTGCTG | 483 |

| | | | |
|---|---|---|---|
| N.lact | 207 | GACGCCGATCCCGACCATCCGGCGCGGGTACGCCGGG | 243 |
| S.clav | 201 | CTCGCCCGTCCCCACCATGCGCCGCGGCTTCACCGGG | 237 |
| pJAR2-4 | 207 | GACGCCGATCCCGACCATGCGCCGCGGCTTCACCGGG | 243 |

| | | | |
|---|---|---|---|
| N.lact | 529 | GAGCAGCCGCTGCGGATGGCCCCGCACTACGACCTCTC | 566 |
| S.clav | 523 | GAGCAGCCCCTGCGGATGGCGCCGCACTACGACCTGTC | 560 |
| pJAR2-6 | 529 | GAGCAGCCGCTGCGGATGGCGCCGCACTACGACCTGTC | 566 |

| | | | |
|---|---|---|---|
| N.lact | 457 | CGCCTTCCTCGACTGCGAACCCCTGCTGCGCCTGCGCT | 494 |
| S.clav | 451 | GGCCTTCCTCGACTGCGAGCCGCTGCTGCGGTTCCGCT | 489 |
| pJAR3-10 | 457 | CGCCTTCCTCGACTGCGAACCGCTGCTGCGGTTCCGCT | 494 |

| | | | |
|---|---|---|---|
| N.lact | 280 | GCAAGTACACCGACTACTCGATGTCGTACTCGATGGGCA | 319 |
| S.clav | 276 | GCAGCTACTCCGACTACTCGATGTGCTACTCGATGGGCA | 313 |
| pJAR4-9 | 280 | GCAAGTACACCGACTACTCGATGTGCTACTCGATGGGCA | 319 |

PENICILLIN CONVERSION

The present application claims priority to U.S. Ser. No. 60/082,800, filed Apr. 23, 1998, the entire contents of which are incorporated herein by reference.

BACKGROUND OF THE INVENTION

Penicillin began the antibiotic revolution. Providing the first real weapon against microbial infections, penicillin (see FIG. 1) first appeared to be a "magic bullet" that would cure all of man's ills. Infectious microbes soon developed resistance to penicillins, however. Great efforts in the pharmaceutical industry have focussed and still focus on the development of alternative antibiotics. One of the most useful families of agents is the cephalosporins (see FIG. 2).

The first cephalosporin, cephalosporin C, was isolated from *Cephalosporium acremonium* (also known as *Acremonium chrysogenum*) in 1954. *C. acremonium* produces cephalosporin C by first synthesizing penicillin N, and then converting this penicillin into cephalosporin C according to the pathway presented in FIG. 3. As shown in FIG. 3, penicillin N is first converted to deacetoxycephalosporin C (DAOC) through oxidative expansion catalyzed by an enzyme known as "DAOC synthase" (DAOCS), or "expandase". A hydroxylase activity, which in *C. acremonium* is part of the same DAOCS enzyme, then converts the DAOC to deacetylcephalosporin C (DAC). In the final step of the conversion, an acetyl transferase substitutes an acetoxy group for the DAC hydroxyl and thereby produces cephalosporin C.

Further study revealed that *C. acremonium* is not the only organism that produces cephalosporins from penicillin N. In particular, *S. clavuligerus* also has both expandase and hydroxylase activities, which activities are separable from one another in this organism. Unfortunately, however, no organism has been identified that naturally produces any commercially useful cephalosporin. Commercially useful cephalosporins (see, for example, FIG. 2B) are typically produced by chemical ring expansion of, for example, penicillin G to yield deacetoxycephalosporin G. Other cephalosporins can then be produced through enzymatic removal of the deacetoxycephalosporin G side chain (phenylacetyl) and substitution of a different side chain. The multi-step chemical ring expansion process is time consuming, expensive, and polluting.

Alternatively, commercially useful cephalosporins could be produced by isolating either the DAOC or the DAC intermediate from *C. acremonium* or *S. clavuligerus* fermentations, and chemically treating the isolate to eliminate the D-α-aminoadipyl side chain and produce a substrate (7-aminodeacetoxycephalosporanic acid [7-ADCA] or 7-aminodeacetylcephalosporanic acid [7-ADAC]) that can subsequently be chemically treated to generate a medically useful cephalosporin (see FIG. 4). Although it avoids the chemical ring expansion step, this strategy is also expensive, since the levels of DAOC or DAC that naturally accumulate are small. There is a need for an improved system for producing cephalosporins.

In particular, there is a need to develop a system that allows cephalosporin production from a penicillin other than penicillin N. Preferably, the system would allow cephalosporin production from an inexpensive penicillin such as penicillin G or penicillin V. As shown in FIG. 5, penicillin G conversion would produce intermediates (deacetoxycephalosporin G [DAOG], deacetylcephalosporin G [DAG]) that could be treated with penicillin acylase to produce the same 7-ADCA or 7-ADAC substrates mentioned above.

Various efforts have been made to utilize the *C. acremonium* or *S. clavuligerus* expandase enzyme either alone or with a hydroxylase enzyme to convert penicillins other than penicillin N into a cephalosporin or cephalosporin intermediate or substrate. Such efforts have almost uniformly failed. Many researchers have reported that the *C. acremonium* and *S. clavuligerus* expandase enzymes have very narrow specificity and fails to expand penicillins other than penicillin N and certain very close relatives.

For example, Kohsaka and Demain, the original discoverers of *C. acremonium* expandase, have reported that only penicillin N, and not penicillin G or 6-aminopenicillanic acid (6-APA), are substrates for expandase activity in crude extracts (Kohsaka et al., *Biochem. Biophys. Res. Commun.* 70(2):1976:465–473, 1976; Demain et al., U.S. Pat. No. 4,178,210, issued Dec. 11, 1979). Further work by this group has demonstrated that partially purified enzyme does not expand adipyl-6-APA, ampicillin, or penicillin G (Kupka et al., *FEMS Microbiol. Lett.* 16:1–6, 1983).

Similarly, researchers have reported that the *S. clavuligerus* expandase expands the ring of penicillin N, but not that of at least twenty other penicillins, including penicillin G, penicillin V, penicillin K, penicillin dihydroF, adipyl-6-APA, m-carboxyphenylacetyl-6-APA, ampicillin, butyryl-6-APA, D-glutamyl-6-APA, and ampicillin (Jensen et al., *J. Antibiot.* 35:1351–1360, 1982; Dotzlaf et al., *J. Biol. Chem.* 264:10219–10227, 1989; Yeh et al. in 50 *Years of Penicillin: History and Trends* [Kleinkauf et al., eds.], Public, Prague, pp. 208–223, 1994; Maeda et al., *Enzyme Microb. Technol.* 17:231–234, 1995).

One group has reported that *Penicillium chrysogenum* cells that have been engineered to express the *S. clavuligerus* expandase gene can produce adipyl-7-aminodeacetoxycephalosporanic acid (adipyl-7-ADCA) when grown in the presence of adipic acid (Conder et al., U.S. Pat. No. 5,318,896, issued Jun. 7, 1995; Crawford et al., *Bio/Technol.* 13:58–62, 1995). *P. chrysogenum* cells are capable of converting adipic acid to adipyl-6-APA; the observation of adipyl-7-ADCA production by the recombinant cells therefore suggests that the *S. clavuligerus* expandase, when expressed in *P. chrysogenum* cells, may be able to expand the endogenous adipyl-6-APA.

A small number of other studies have reported some ability of *S. clavuligerus* or *C. acremonium* expandase enzymes to expand D-carboxymethylcysteinyl-6-APA, a very close relative to penicillin N (Bowers et al., *Biochem. Biophys. Res. Commun.* 120:607–614, 1984) and adipyl-6-APA (Baldwin et al., *J. Chem. Soc. Chem. Commun.* 1466:374–375, 1987; Shibata et al., *Bioorg. Med. Chem. Lett.* 6:1579–1584, 1996), in vitro. One group (Baldwin et al., *J. Chem. Soc. Chem. Commun.* 1466:374–375, 1987) has also suggested that m-carboxyphenylacetyl-6-APA, D-glutamyl-6-APA, and glutamyl-6-APA might also serve as in vitro substrates, albeit at very low levels. Subsequent work failed to confirm these reports, however (Yeh et al., in 50 *Years of Penicillin: History and Trends* [*Kleinkauf et al, eds*], Public, Prague, pp. 208–223, 1994).

One brief abstract reported that a recombinant form of *S. clavuligerus* expandase, when expressed in and purified from *Escherichia coli*, might be able to expand penicillin G (Baldwin et al., Abstract P-262, Abstracts of the 7th International Symposium on Genetics of Industrial Microorganisms, Montreal, Jun. 26–Jul. 1, 1994, pg. 184). Unfortunately, the report did not contain sufficient detail to allow ready duplication of the results and no subsequent work has confirmed the finding.

Thus, the prior art attempts to develop an improved system for producing cephalosporins from penicillins other than penicillin N have generally failed. In particular, efforts to develop a system that utilizes penicillin G as a substrate have been unsuccessful. There remains a need for development of improved systems for converting penicillins other than penicillin N. Particularly desirable systems would utilize exogenously-added penicillins rather than relying on in vivo microbial penicillin production. Particularly preferred systems would obviate the need for multi-step chemical ring expansion methods.

SUMMARY OF THE INVENTION

The present invention provides techniques and reagents for the bioconversion of penicillins other than penicillin N into cephalosporins or cephalosporin precursors. The inventive conversion system allows biological ring expansion of penicillin substrates such as penicillin G, and replaces the multi-step chemical ring expansion process currently performed in industry. The inventive system can utilize growing or resting cells (free or immobilized), or isolated expandase (crude or purified), and is capable of converting exogenously-added penicillins. The inventive system can be applied to any penicillin substrate, including natural penicillins (e.g., penicillin G), biosynthetic penicillins (e.g., penicillin V), semisynthetic penicillins (e.g., ampicillin), and/or synthetic penicillins.

Definitions

"Cephalosporin precursor"—The term "cephalosporin precursor", as used herein, refers to a compound that, through one or more chemical reactions not relying on an expandase, can be converted into a cephalosporin. This term is intended to encompass many compounds that are also cephalosporins, so long as they are convertible into other cephalosporins. Preferred cephalosporin precursors have the structure depicted in FIG. 2A, and include 7-ADCA, 7-ADAC, 7-ACA, DAOG, DAG, cephalosporin G, and cephamycin G. DAOG and DAG are particularly preferred.

"Exogenous substrate"—The term "exogenous substrate", as used herein, refers to a substrate that is added to a reaction and is not produced internally by a cell producing expandase. That is, when the expansion reaction occurs inside a cell that produces both the expandase and the penicillin substrate on which the expandase acts, that substrate is an "endogenous" substrate. By contrast, if the penicillin substrate is added e.g., to cells producing the expandase, that substrate is exogenous, even if it is the same chemical compound that is being (or could be) produced by the cell.

"Isolated"—The term "isolated", when applied to a compound that exists in nature, means (i) separated from at least some of the components with which it is normally associated in nature; and/or (ii) produced or prepared through a process (e.g., involving in vitro synthetic chemistry) that does not occur in nature.

"Purified"—A compound is considered "purified" when it is at least about 50% pure, preferably at least 70–80% pure, more preferably at least about 90% pure, yet more preferably at least 95% pure, and most preferably at least 99% pure.

"Recombinant"—The term "recombinant", as used herein, means produced through a method relying on techniques of recombinant DNA technology. For example, an expandase gene is separated from DNA with which is normally associated in nature and is introduced into an expression vector, the gene in the context of the vector is a "recombinant" gene. Similarly, the protein expressed from the gene is a "recombinant" protein.

DESCRIPTION OF THE DRAWINGS

FIG. 1B shows $R_1$ groups present in different penicillins.

FIG. 4, Panels A and B depict chemical treatment of the intermediates DAOC and DAC, respectively, to produce cephalosporin precursors 7-ADCA and 7-ADAC.

FIG. 21 shows the sequences of crossover junctions of hybrid expandase genes obtained in DH5α cells.

DESCRIPTION OF CERTAIN PREFERRED EMBODIMENTS

Figure 1A:
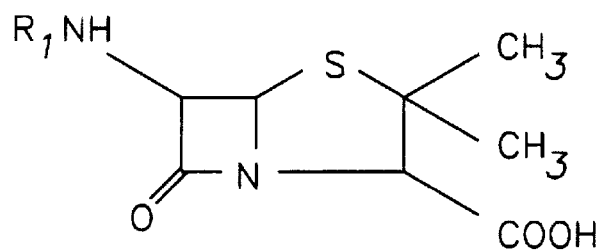
FIG. 1A presents a generalized structure of penicillins.
Figure 2A:
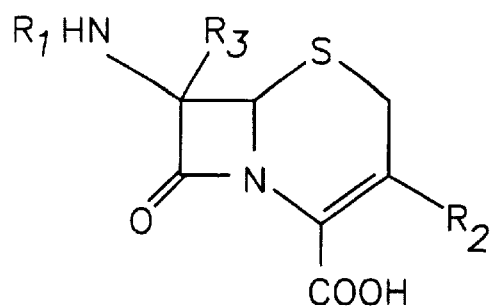
FIG. 2A presents a generalized structure of cephalosporins.
Figure 2B:
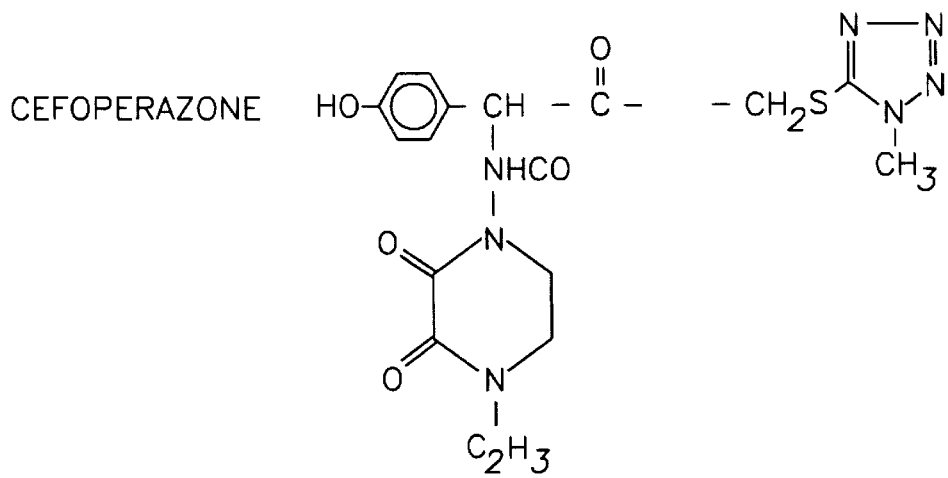
FIG. 2B shows $R_1$ and $R_2$ groups present in certain different cephalosporins.
Figure 2:
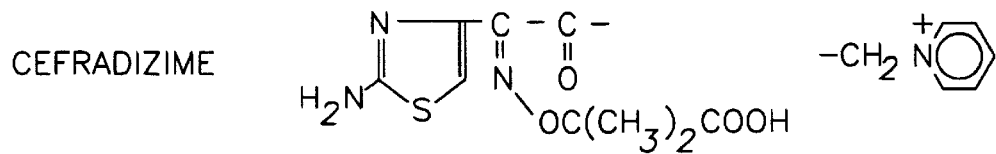
Figure 3:
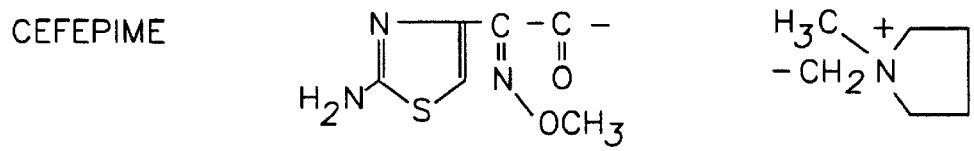
FIG. 3 presents a portion of the cephalosporin C biosynthetic pathway utilized by C. acremonium to produce cephalosporin C from endogenous penicillin N.
Figure 3:
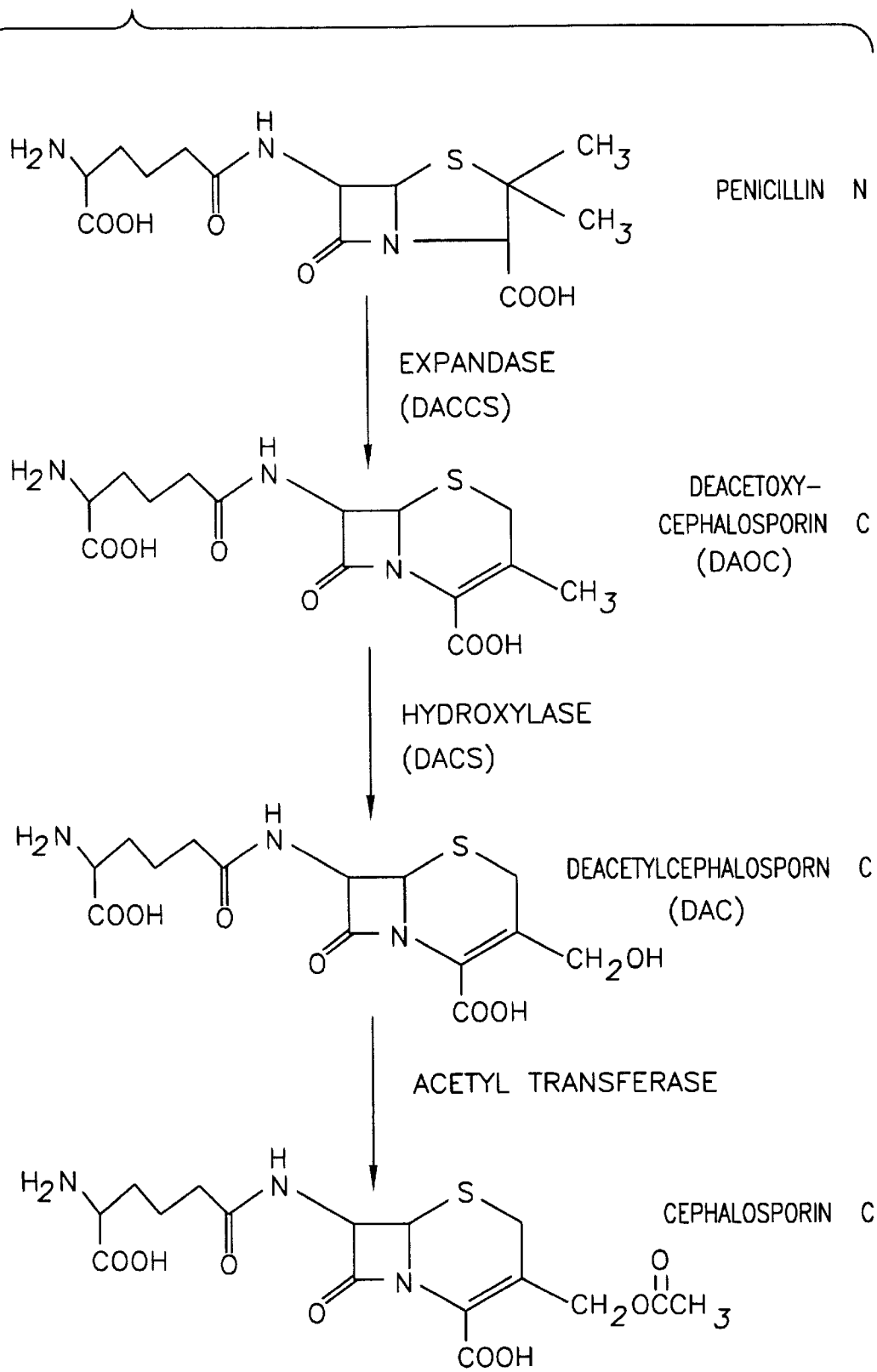
Figure 5:
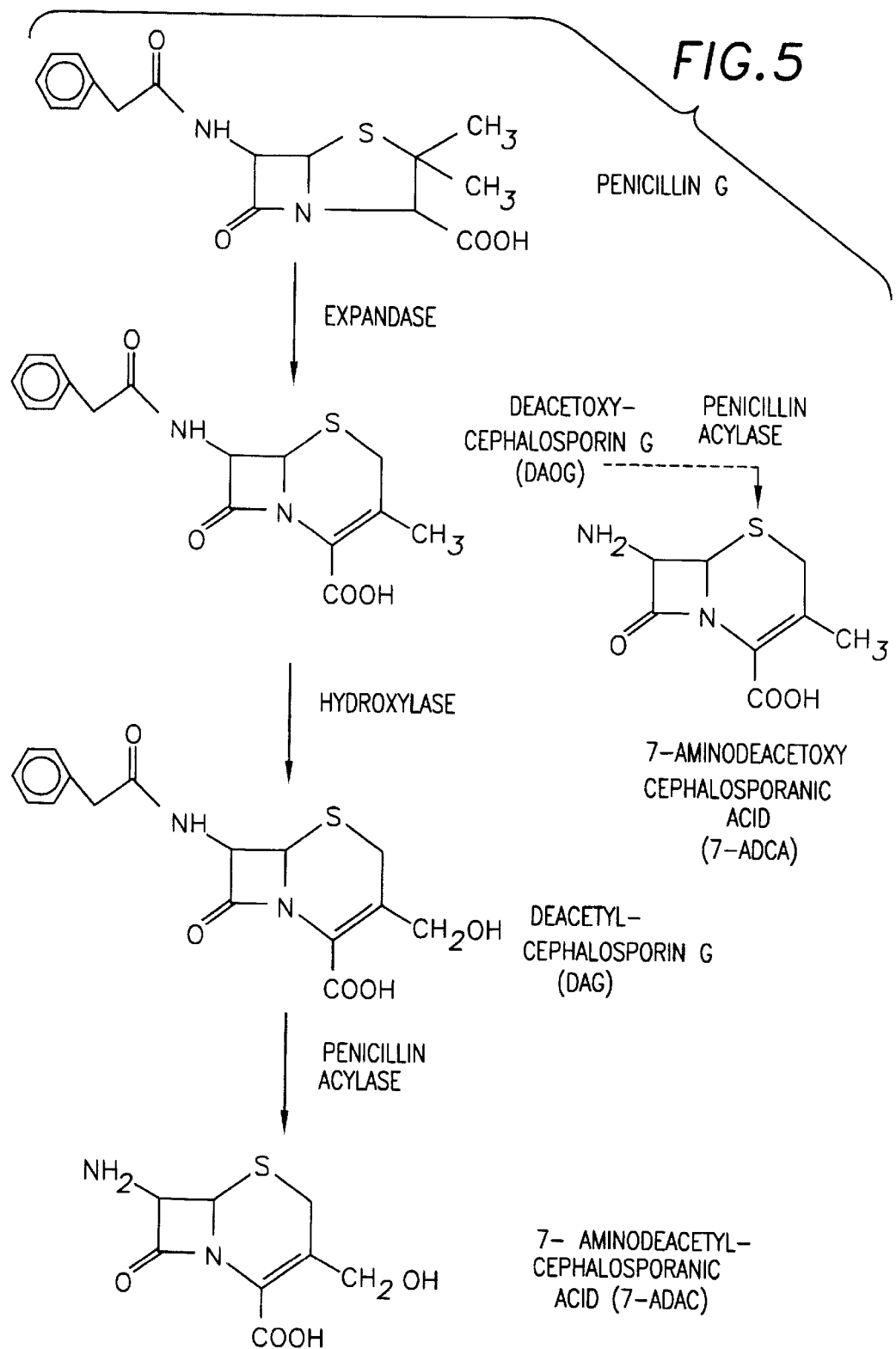
FIG. 5 depicts production of 7-ADCA and 7-ADAC through a penicillin G biological ring expansion pathway, followed by enzymatic removal of the phenylacetyl side chain.

As mentioned above, the present invention provides an improved system for the conversion of penicillins into cephalosporins or cephalosporin precursors. In particular, the invention defines reaction conditions under which expandase-producing cells, or extracts or enzymes thereof, convert penicillins other than penicillin N or its close relatives into cephalosporins.

One aspect of the invention involves the definition of reaction conditions that allow such conversion, and the concomitant identification of factors that affect the success and/or efficiency of such conversion. Another aspect of the invention provides compositions and/or methods for achieving such conversion. In general, the invention utilizes (i) an expandase source; (ii) a penicillin substrate; and (iii) reaction conditions that allow conversion of the penicillin substrate into a cephalosporin or cephalosporin precursor. Each of these inventive components is discussed in more detail below.

Expandase Source

The present invention demonstrates that, under appropriate reaction conditions, S. clavuligerus cells (whether they be growing, resting, or immobilized) or cell extracts (free or immobilized) are an appropriate source of expandase activity for converting penicillin substrates other than penicillin N to cephalosporins (see Examples). In light of these teachings, those of ordinary skill in the art will appreciate that S. clavuligerus expandase is an appropriate enzyme for use in accordance with the present invention, regardless of its form or mode of preparation.

For example, S. clavuligerus expandase may be purified from S. clavuligerus cells according to known techniques (see, for example, Jensen et al., Antimicrob. Agents Chemother. 24:307–312, 1983; Dotzlaf, et al., J. Biol. Chem.264:10219–10227, 1983 incorporated herein by reference) and utilized in the practice of the present invention. Moreover, the gene for the S. clavuligerus expandase has been cloned (Kovacevic, et al., J. Bacteriol. 177:754–760, 1989), and may be introduced into an expression construct that allows expandase production in any of a variety of host cells from which it can be used as a cellular product, prepared as an extract, or purified for use in inventive reactions.

Techniques for introducing cloned genes into expression constructs are well known in the art (see, for example, Sambrook et al., Molecular Cloning: A Laboratory Manual, Cold Spring Harbor Laboratory Press, Cold Spring Harbor, New York, 1989, incorporated herein by reference). So long as the expandase protein is produced in the host cell, the expression construct, its mode of preparation (e.g., the selection of regulatory sequences such as the gene promoter, upstream regulatory elements, splicing signals, RNA processing signals, etc.), and its manner of introduction into the host cell (e.g., by transformation, transfection, infection, injection, electroporation, etc.) are appropriate according to the present invention. In certain embodiments of the invention, the expression construct may be engineered to allow secretion of the expandase protein into the cell supernatant.

Preferred host cells in which S. clavuligerus expandase is preferably expressed include, but are not limited to bacterial cells, fungal cells, insect cells, plant cells or vertebrate (including mammalian) cells. Those of ordinary skill in the art will recognize that expression vectors that direct production of a desired protein in a particular kin of host cell are readily available for a wide range of host cells (see, for example, Sambrook et al., Molecular Cloning: A Laboratory Manual, Cold Spring Harbor Laboratories Press, Cold Spring Harbor, N.Y., 1989, incorporated herein by reference).

Moreover, the expressed expandase need not be isolated or purified from the host cell in order to be used in accordance with the present invention. That is, as discussed above and in the Examples, S. clavuligerus cells themselves, whether growing, resting, or immobilized in certain polymeric matrices, are appropriate sources of expandase for use in the practice of the present invention. Host cells expressing a recombinant S. clavuligerus gene can readily be assayed as described herein to identify those that are useful sources of expandase for use in the practice of the present invention.

Those of ordinary skill in the art will readily appreciate that S. clavuligerus expandase is not the only expandase that is useful in accordance with the present invention. For example, a wide variety of organisms such as unicellular bacteria (e.g., Xanthomonas lactamgena, Lysobacter lactamgenus, Flavobacterium sp., Flavobacterium chitinovorum, etc.), filamentous bacteria (e.g., Streptomyces organanensis, Nocardia lactamdurans, Streptomyces lipmanii, Streptomyces jumonjinensis, Streptomyces wadayamensis, Streptomyces cattleya, Streptomyces lactamgens, Streptomyces fradiae, Streptomyces griseus,

*Streptomyces olivaceus, Streptomyces sp.*), and filamentous fungi (e.g., *C. acremonium*) are expected to produce proteins with expandase activity, at least when assayed on penicillin N (see, for example, Caswell et al., in 50 *Years of Penicillin: History and Trends,* [*Kleinkauf et al., eds*]., Public, Prague, p.135, 1994; Kohsaka, et al, *Biochem. Biophys. Res. Comm.,* 70:465–473; Stapley et al. *Antimicrob. Agents Chemother.* 2:122–131, 1972; Cortes et al., *Biochem. Soc. Transac.* 12:863–864, 1984). Any such cells, or extracts or expandases prepared from such cells, may be screened according to the procedures described herein to identify those with an ability to expand non-penicillin N substrates. Furthermore, desirable expandases defined in such cells may be expressed in host cells as described above with respect to *S. clavuligerus* expandase, and the host cells, host cell extracts, or isolated or purified host-cell-expressed expandase, may be employed in the practice of the present invention.

According to the present invention, an expandase-producing cell is a suitable source of expandase if, when provided with an exogenous penicillin substrate, preferably penicillin G or penicillin V, it produces a compound that creates a zone of inhibition when tested in paper disc-agar diffusion assay containing penicillinase as described herein. Alternatively or additionally, an expandase-producing cell is a suitable source of expandase if, when tested as described herein, it accomplishes sufficient expansion of a penicillin substrate, preferably penicillin G or penicillin V, that at least one peak corresponding to a cephalosporin precursor (preferably DAOG, DAG, cephalosporin G, and/or cephamycin G) is observed in HPLC.

In general, where intact cells are utilized in the inventive system, they may be growing, they may be resting, and they may be either free or immobilized (e.g., in a polymeric matrix). Those of ordinary skill in the art will appreciate that any of a variety of matrices or immobilization techniques may be employed to immobilize cells (see, for example, *Enzymes and Immobilized Cells In Biotechnology* [Laskin, ed], Benjamin Cummings Publishing Company, Menlo Park, Calif., 1985, incorporated herein by reference), so long as the expandase remains sufficiently active after immobilization. PEI-barium alginate is particularly preferred, especially for use with *S. clavuligerus* cells (see Example 5). Of course, the utility of a particular polymeric matrix in any given application may depend to a certain extent on the nature and characteristics of the cells to be embedded therein. It is well within the province of one of ordinary skill in the art to screen a variety of polymeric matrices as described herein to identify one that is suitable for use with cells other than *S. clavuligerus* cells.

Although the above discussion has focussed on expandases produced by cellular sources, and it is expected that such will be the most common form of expandase utilized in the present invention, it will be understood that any expandase source, including, for example, protein wholly or partially synthesized through in vitro chemical or biochemical methods is also acceptable.

Furthermore, those of ordinary skill in the art will appreciate that, once an expandase gene is cloned, various modifications or alterations to gene sequence, resulting in modifications or alterations of protein sequence, can readily be made using standard recombinant techniques such as, for example, site-directed mutagenesis, polymerase chain reaction mutagenesis, exo- or endo-nuclease digestion, gene shuffling (i.e., equal homologous recombination) (see, for example, Example 6), etc. Such modifications or alterations include, for example, production of fusion proteins; addition, deletion, or substitution of one or more amino acids; etc. Alternatively or additionally, the chemical structure of a particular expandase protein may be altered through modification of the protein after it is made, e.g., through proteolytic cleavage or chemical modification. Expandase enzymes with altered structure as compared with expandases that occur in nature are useful in the practice of the present invention so long as they retain the ability to expand penicillin substrates as described herein.

Penicillins

As discussed above, the present invention provides a system for expansion of penicillins other than penicillin N. Penicillin substrates for use in the practice of the present invention include all natural penicillins (i.e., penicillins that are naturally produced by *P. chrysogenum*—e.g., penicillin G), biosynthetic penicillins (i.e., penicillins that are produced by *P. chrysogenum* through directed biosynthesis when a side chain acid is added to the medium—e.g., penicillin V), semi-synthetic penicillins (i.e., penicillins that are made by chemical means from natural or biosynthetic penicillins—e.g., ampicillin), and synthetic penicillins (i.e., penicillins that are made wholly synthetically), other than penicillin N. For example, preferred penicillin substrates include, but are in no way limited to, adipyl-6-APA, amoxicillin, ampicillin, butyryl-6-APA, decanoyl-6-APA, heptanoyl-6-APA, hexanoyl-6-APA, nonanoyl-6-APA, octanoyl-6-APA, penicillin F, penicillin G, penicillin V, penicillin mX, penicillin X, 2-thiopheynlacetyl-6-APA, and valeryl-6-APA. Particularly preferred penicillins include penicillin G, penicillin mK, penicillin X, penicillin V, ampicillin, amoxicillin, and 2-thiophenylacetyl-6-APA. Most preferred are penicillins G and V, which are articles of commerce and are therefore inexpensive.

Reaction Conditions

As described herein, one important aspect of the present invention is the definition of reaction conditions under which expandases that naturally operate on penicillin N will act on other penicillins, preferably when those penicillins are added as exogenous substrates (i.e., are not produced by the cells producing the expandase). Standard reaction conditions for expansion of penicillin N are well known in the art (see, for example, Maeda et al., *Enzyme Microb. Technol.* 17:231–34, 1995; Cortes et al., *Biochem. Soc. Transac.* 12:863–864, 1984; Jensen et al., *J. Antibiot.* 35:1351–1360, 1982; Shen et al., *Enzyme Microb. Technol.* 6:402–404, 1984; Dotzlaf et al., *J. Biol. Chem.* 264:10219–10227, 1989). As the present invention demonstrates, however, such conditions are likely not to be useful for conversion of substrates other than penicillin N.

According to the present invention, optimal reaction conditions for a particular expandase source and penicillin substrate can be identified by varying the presence or amount of one or more of: α-ketoglutarate, $Fe^{2+}$, ascorbate, reducing agents (such as, for example, dithiothreitol (DDT) or β-mercaptoethanol (βME)), and ATP. Also, the characteristics and amount of the expandase source can be varied. For example, expandase can be provided from cells grown to different densities or collected at different stages of growth. Alternatively or additionally, the purity or concentration of the expandase preparation may be varied. Also, variations can be made in the concentration of the substrate and the temperature and pH of the reaction. Buffer selection may also be adjusted. Alternatively or additionally, where the expandase source is cells or is extract or purified protein prepared from cells, the conditions under which the cells are grown (e.g., carbon source, nitrogen source, source of phosphorus and other minerals, availability of oxygen, etc) can be adjusted. As discussed herein, the ideal reaction conditions may vary depending, for example, on the nature (e.g., resting cells, growing cells, immobilized cells, purified enzyme, immobilized enzyme, etc.) of the expandase source.

Preferred buffers for use in inventive expandase reactions include, but are not limited to, Tris, MOPS, HEPES, phosphate buffers, etc. Buffers are preferably employed at concentrations within the rage of about 50–200 mM, and pHs within the range of about 5.0–9.0, depending on the particular buffer. Tris is preferably employed at a pH within the range of 6.5–9.0; HEPES within the range of 6.0–8.5; MOPS within the range of 5.5–8.0; and phosphate within the range of 5.0–7.5. Particularly preferred reactions utilize, 50 mM Tris-HCl at pH 7.4, 50 mM MOPS at pH 6.5, or 50 mM HEPES at pH 6.5 are preferred, with 50 mM MOPS at pH 6.5 or 50 mM HEPES at pH 6.5 being especially preferred.

Ascorbic acid, when it is utilized, is preferably provided in a concentration within the range of 0.8–50 mM, preferably 2–8 mM, and most preferably about 4 mM. As demonstrated herein, ascorbic acid is not required in inventive reactions, particularly in reactions employing resting cells.

α-Ketoglutarate is preferably provided in a concentration within the range of 0–4 mM, preferably about 0.5–2.0 mM, and most preferably about 1.28–1.5 mM.

Preferred reducing agents include DTT and βME. As demonstrated herein, such reagents are not essential to expandase reactions, and may actually inhibit reactions with resting cells. Thus, reducing agents are preferably left out of inventive expandase reactions, particularly those employing resting cells. Alternatively, they may be provided at concentrations within the range of about 0.1–14 mM, preferably 14 mM.

Iron concentration in the inventive expandase reactions is preferably maintained within the range of 0–4 mM, preferably about 0.5–2.5 mM, and most preferably 1.8–2.2 mM.

ATP need not be provided in preferred reactions according to the present invention. Where it is provided, it is preferably provided at a concentration less than about 3.5 mM, preferably within the range of about 0–3 mM, and most preferably within the range of about 0.14–2.4 mM.

The penicillin substrate is preferably provided at a high concentration (e.g., more than about 2 mg/ml, preferably more than about 5 mg/ml) in order to produce the largest possible amount of cephalosporin, or at a low concentration (e.g., less than about 2 mg/ml, preferably less than about 1 mg/ml, and most preferably less than about 0.25 mg/ml) in order to achieve a higher efficiency of conversion.

Other salts or reagents that can be employed in certain expandase reactions in accordance with the present invention include, for example, KCl (preferably at a concentration within the range of 0–8 mM, preferably being excluded from reactions with resting cells); $MgSO_4$ or other $Mg^{2+}$ source (preferably at a concentration within the range of 0–8 mM, preferably being excluded from reactions with resting cells), etc.

Expandase is preferably present at the highest concentration possible without inhibiting the reaction (e.g., due to contaminants—including whole cells—in the expandase preparation). Where expandase is provided in the form of cells, the cells are preferably utilized at the lowest possible biomass (e.g., less than about 6 g, wet weight/10 ml solution, preferably within the range of about 0.5–4.0 g wet weight/10 ml solution, and most preferably about 1–3 g, wet weight/10 ml solution).

Also, where the expandase is provided from a cellular source (whether it is provided in cellular form or in isolated or purified form), the cells producing the expandase are preferably grown under conditions of nutrient imbalance and/or of low growth rate, as such conditions are expected to maximize antibiotic production. In particular, the cells are preferably grown in the presence of a stressing agent such as an alcohol (e.g., methanol or ethanol, preferably in the range of 1–2%) or heat (i.e., under conditions of heat shock).

Those of ordinary skill in the art will readily recognize that any of a variety of other reaction and/or preparation conditions can readily be varied and tested according to the procedures set forth herein without undue experimentation. According to the present invention, reaction conditions that produce a zone of inhibition in the growth assays described herein, or produce one or more cephalosporin precursor peaks on HPLC, are desirable for use in accordance with the present invention.

Diversification of Cephalosporin Precursor

A wide variety of chemical reactions are known in the art that can be employed to diversify a cephalosporin precursor, produced as described herein, to provide a desirable cephalosporin. In particular, many approaches have been established for introducing different chemical groups at the 3- and 7-positions of the cephalosporin ring system (see, for example, Durckheimer et al., *Adv. Drug. Res.* 17:61, 1988, and references cited therein; *Drugs* 34 (Suppl. 2), 1987, each of which is incorporated herein by reference).

Several particularly useful third- and fourth-generation cephalosporins (e.g., cefotaxime) include a 2-aminothiazol-4-yl-acetamido side chain combined with a syn-alkoxyimino group. A wide variety of modifying reactions are known that can be performed on such structures, or that can generate related compounds from a cephalosporin precursor such as 7-ACA (see summary in Kirrstetter et al., *Die Pharmazie*, 44:177–184, 1989, incorporated herein by reference).

Other useful cephalosporins include those with polar pyridino or quaternary amino substitutes at C-3' and a neutral or an acidic oxime group in the 7-side chain. Once again, syntheses have been worked out for a wide variety of related compounds (see, for example, Durckheimer et al., *Adv. Drug. Res.* 17:61, 1988; *Drugs of the Future* 13:271, 1988).

Those of ordinary skill in the art will recognize that any available technique for generating cephalosporins from cephalosporin precursors provided as described herein is useful in the practice of the present invention. The reactions employed to generate the final cephalosporins are not intended to limit the scope of the invention.

EXAMPLES

Example 1

Penicillin Ring Expansion by *S. clavuligerus* Resting Cells and Cell-Free Extracts Materials and Methods Microorganism: We utilized a known *S. clavuligerus* mutant, known as "NP1", that does not naturally produce significant levels of cephalosporins, but is known to produce cephalosporin C when fed exogenous penicillin N (see Mahro et al., *Appl. Microbiol. Biotechnol.* 27:272–275, 1987). The ability of this mutant to produce cephalosporin C under these conditions indicates that the strain's expandase is functional.

Media and Culture Conditions: Mycelia were obtained using 250 ml baffled flasks containing 40 ml of MST medium: 1% soluble starch (Sigma Chemical Co., St. Louis, Mo.); 3% Trypticase Soy Broth Without Dextrose (BBL, Cockeysville, Md.); 90 mM MOPS buffer, pH adjusted to 7.0 before autoclaving. Each flask was inoculated with 50 µl of a spore suspension (prepared and stored at −80° C. in 20% glycerol) and incubated at 30° C., 250 rpm for 48 h.

Materials: Penicillin G, ascorbic acid and α-ketoglutaric acid were from Sigma Chemical Company (St. Louis, Mo.). Deacetoxycephalosporin G was from Antibióticos, S.A. (León, Spain) and Bacto-Penase from Difco Laboratories (Detroit, Mich.).

Preparation of Cell-free Extracts: Fermentation broths were centrifuged at 8,000×g and 4° C. for 10 min. Pellets were washed twice using 50 mM Tris-HCl supplemented with 0.1 mM dithiothreitol (DTT). The cells were resuspended in the same buffer and disrupted by four 25-sec. sonication treatments (power setting 5 and duty cycle 50%), in an ice-water bath using a Branson 350 sonifier (Branson Sonic Power Co., Danbury, Conn.). Cell debris was removed by centrifugation (14,000×g, 30 min., 4° C.). The resulting extracts containing 8–10 mg protein/ml were placed on ice and utilized immediately. Protein concentrations were measured using the Bio-Rad protein assay (Bio-Rad, Hercules, Calif.). Bovine serum albumin was used as standard.

Resting Cells: From a seed culture (in MST), 0.5 ml was transferred to new flasks containing 40 ml of the same medium. Cells were grown at 30° C., 250 rpm for 24 h. Mycelia from each flask were washed twice, and finally, resuspended in 10 ml of distilled water. Four ml of this cell suspension were used in the reaction mixture.

Ring Expansion Reaction: We defined ring expansion reaction conditions as modifications of the standard reaction mixture for expandase reactions described by Maeda et al. (Maeda et al., *Enzyme Microb. Technol.* 17:231–34, 1995) except that penicillin G was used a substrate instead of penicillin N. Additions were made following the order established by Shen et al. (Shen et al., *Enzyme Microb. Technol.* 6:402–404, 1984. Reaction mixtures were incubated in test tubes (cell-free extract) or 250 ml baffled flasks (resting cells) at 220 rpm, 30° C. Reactions containing the protein extract were stopped at various times (see Table 1 and Figure Legends) by mixing 0.5 ml of assay solution with 0.5 ml of methanol. In the case of resting cells, samples were centrifuged to remove cells and supernatants were transferred to new tubes. Expandase activity was detected by paper disc-agar diffusion bioassay.

Detection of Expandase Activity: As mentioned above, expandase activity was detected by assaying production of a growth-inhibitory zone in a paper disc-agar diffusion bioassay. Paper discs were saturated with 200 µl of the reaction mixture (cell-free extracts or supernatant (resting cells) as follows. Two discs were superimposed and four 50 µl samples were applied. After each application, the discs were allowed to dry for 20 min at 37° C. under a laminar hood and, finally, they were placed on LB (1% tryptone, 0.5% NaCl, 0.5% yeast extract, 0.1% glucose) 0.8% agar medium seeded with *E. coli* ESS (a β-lactam supersensitive mutant), and the plates were incubated overnight at 37° C. The formation of DAOG and/or other cephalosporin(s) was determined by including 50,000 IU/ml of penicillinase (Difco Bacto penase concentrate, Difco Laboratories, Detroit, Mich.) in the assay plates. This penicillinase is a narrow spectrum β-lactamase that attacks penicillins but not cephalosporins. The diameters of zones of growth inhibition were measured and quantified with a calibration curve using DAOG as standard.

Test Substrates: All penicillins used in this work, except penicillin G and ampicillin (Sigma Chemical Co, Mo.), were provided by Saul Wolfe (Simon Fraser University, Canada) or Jose M. Luengo (University of León, Spain), and were synthesized as previously described (Maeda et al., *Enzyme Microb. Technol.* 17:231–34, 1995). DAOG was provided to us by Antibióticos, S. A. (Madrid, Spain).

Results

Penicillin G Ring Expansion by Resting Cells: Prior work had indicated that the thiazolidine ring of penicillin G could not be expanded with cell-free extracts of *S. clavuligerus* (Maeda et al., *Enzyme Microb. Technol.* 17:231–234, 1995). We nonetheless endeavored to define reaction conditions that would allow ring expansion. We began our studies using resting cells instead of cell extracts.

In order to identify useful reaction conditions, we varied the concentrations of $FeSO_4$, α-ketoglutarate, ascorbate, and ATP in our mixtures. We also tested the effect of cell mass in our reactions.

Figure 6:
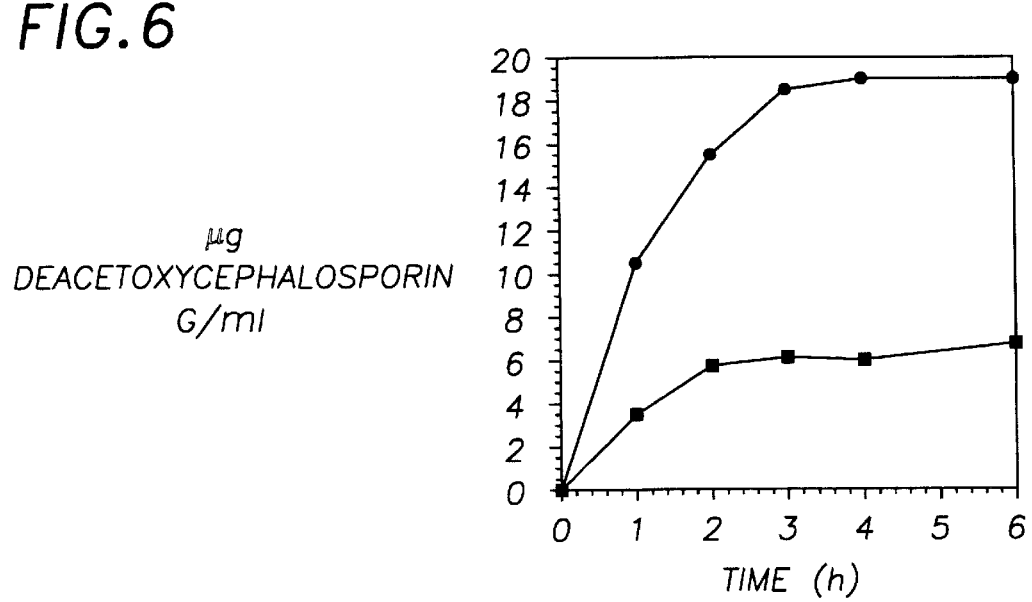
FIG. 6 shows a time course of the ring expansion of penicillin G by resting cells. (●) indicates the successful inventive reaction conditions; (■) indicates reactions that were unsuccessful when utilized in the prior art with cell-free extracts.

The unsuccessful Maeda et al. reactions, which were performed with cell-free extracts and were assayed in a growth inhibition assay that used smaller amount of sample than we utilized in our assays, contained 50 mM Tris-HCl pH 7.4, 8 mM KCl, 8 mM $MgSO_4$, 14 mM DTT, 4 mM ascorbic acid, 0.04 mM $FeSO_4$, 0.64 mM α-ketoglutarate, and 0.28 mM penicillin G. We found that resting cell reaction mixtures containing 45 times as much $Fe^{2+}$ (i.e., 1.8 mM $FeSO_4$) and twice as much α-ketoglutarate (i.e., 1.28 mM α-ketoglutarate) allowed successful expansion of penicillin G by resting cells (see FIG. 6). Using our version of the growth inhibition assay, we found that even the Maeda et al. reaction conditions (■) produced some DAOG (about 6 µg/ml after 3–6 hours of reaction) when employed with resting cells. Resting cells reacted under the inventive conditions (●) produced at least three times as much (about 19 µg/ml after 3–6 hours of reaction).

We further found, as shown below in Table 1, that omission of $Fe^{2+}$, α-ketoglutarate, or ascorbic acid reduced the amount of DAOG produced after two hours of reaction to about 30% of that produced in a complete reaction. On the other hand, omission of ATP, $MgSO_4$, KCl, or DTT did not have a marked negative effect. In fact, omission of DTT actually increased DAOG production approximately 50%. All reactions contained 50 mM Tris-HCl pH 7.4, 13 mg/ml dry cell weight cells, and 2 mg/ml of penicillin G. One ml of sample was taken from each reaction and was centrifuged at 12K rpm for 5 minutes. The supernatants were then transferred to new tubes and 200 µl were used in the bioassay (in other experiments, 100 µl or 150 µl were used).

TABLE 1

Effect of Cofactors of Penicillin G Ring Expansion by Resting Cells

| Cofactor Omitted | µg DAOG/ml |
|---|---|
| None | 10.5 |
| DTT (16 mM) | 15.5 |
| α-ketoglutarate (1.28 mM) | 3.7 |
| $FeSO_4 \cdot 7H_2O$ (1.8 mM) | 3.2 |
| $MgSO_4 \cdot 7H_2O$ (8 mM) | 10.1 |
| KCl (8 mM) | 11.5 |
| Ascorbic acid (4 mM) | 3.0 |
| ATP (0.7 mM) | 10.0 |

Figure 7:
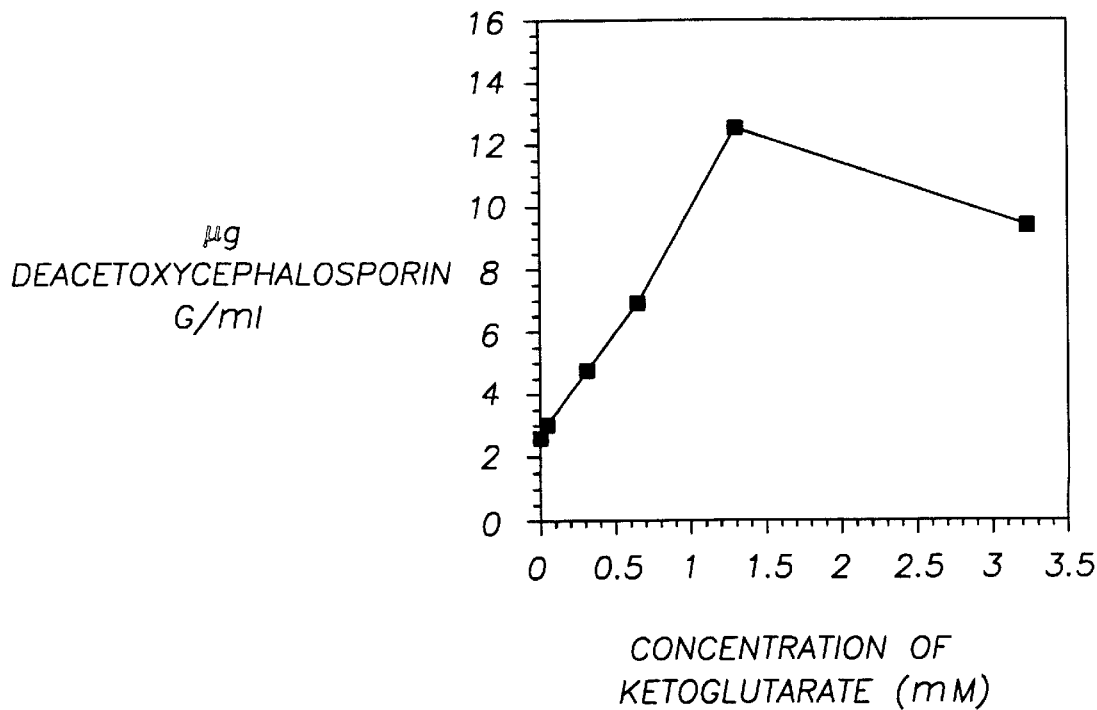
FIG. 7 shows the effect of α-ketoglutarate concentration on ring expansion of penicillin G by resting cells. Reactions contained 50 mM Tris-HCl pH 7.4, 8 mM KCl, 8 mM $MgSO_4$, 4 mM ascorbic acid, 1.8 mM $FeSO_4$, and 2 mg/ml penicillin G. Dry cell weight was 12 mg/ml. Samples were taken at 2 hour and centrifuged at 12K rpm for 5 minutes. 200 µl were used in the bioassay.
Figure 8:
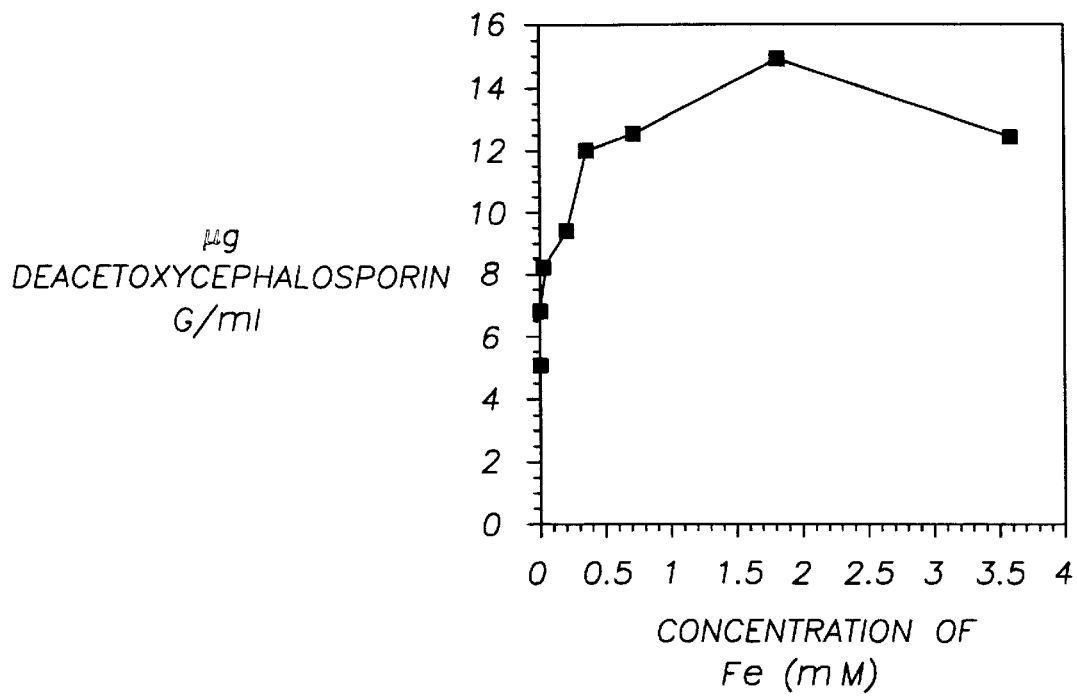
FIG. 8 shows the effect of $Fe^{2+}$ concentration on ring expansion of penicillin G by resting cells. Reactions contained 50 mM Tris-HCl pH 7.4, 8 mM KCl, 8 mM $MgSO_4$, 4 mM ascorbic acid, 1.28 mM α-ketoglutarate, and 2 mg/ml penicillin G. Dry cell weight was 10 mg/ml. Samples were taken at 2 hour and centrifuged at 12K rpm for 5 minutes. 200 µl were used in the bioassay.

When we varied the concentration of individual reaction components in the context of our successful conditions, we found that increasing the α-ketoglutarate concentration from 0.64 mM to 1.28 mM doubled the amount of DAOG produced (see FIG. 7); increasing $Fe^{2+}$ concentration (FIG.

8) or ascorbate concentration (Table 2) also increased DAOG production until optimal reagent levels (about 1.8 mM for $Fe^{2+}$ and 4–8 mM for ascorbate) were reached, but ATP had little effect until high concentrations (around 3.5 mM) began inhibiting the reaction (Table 2). Interestingly, studies of expansion of the penicillin N ring had indicated that ATP stimulated that reaction.

TABLE 2

Effect of Modifications in Ascorbate or ATP Concentration on Penicillin G Ring Expansion by Resting Cells

| Cofactor | Concentration | μg DAOG/ml |
|---|---|---|
| Ascorbate | 0 | 2.4 |
|  | 0.8 | 4.0 |
|  | 2 | 6.0 |
|  | 4 | 6.4 |
|  | 8 | 6.4 |
| ATP | 0 | 6.6 |
|  | 0.14 | 6.4 |
|  | 0.35 | 6.4 |
|  | 0.7 | 6.6 |
|  | 2.4 | 6.6 |
|  | 3.5 | 4.7 |

Figure 9:
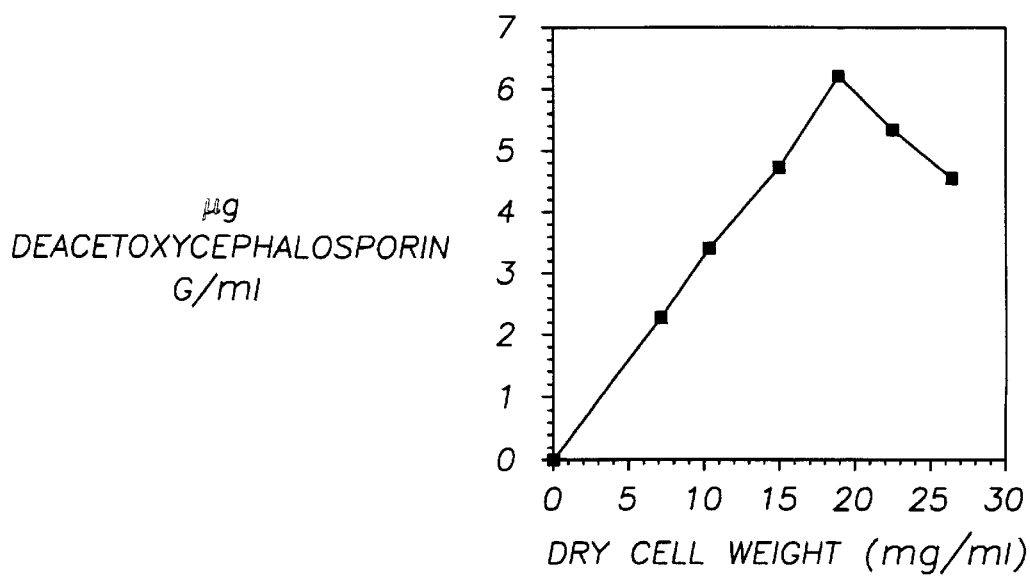
FIG. 9 shows the effect of cell mass concentration on penicillin G ring expansion by resting cells. The reaction contained 50 mM Tris-HCl pH 7.4, 8 mM KCl, 8 mM $MgSO_4$, 4 mM ascorbic acid, 1.8 mM $FeSO_4$, 1.28 mM α-ketoglutarate, and 2 mg/ml penicillin G. Samples were taken at 2 hour and centrifuged at 12K rpm for 5 minutes. 200 µl were used in the bioassay.

We further found that increasing cell mass enhanced the formation of DAOG until an optimum concentration of about 19 mg/ml dry cell weight was reached; higher concentrations inhibited DAOG production, probably due to limited oxygen supply (FIG. 9).

Figure 10:
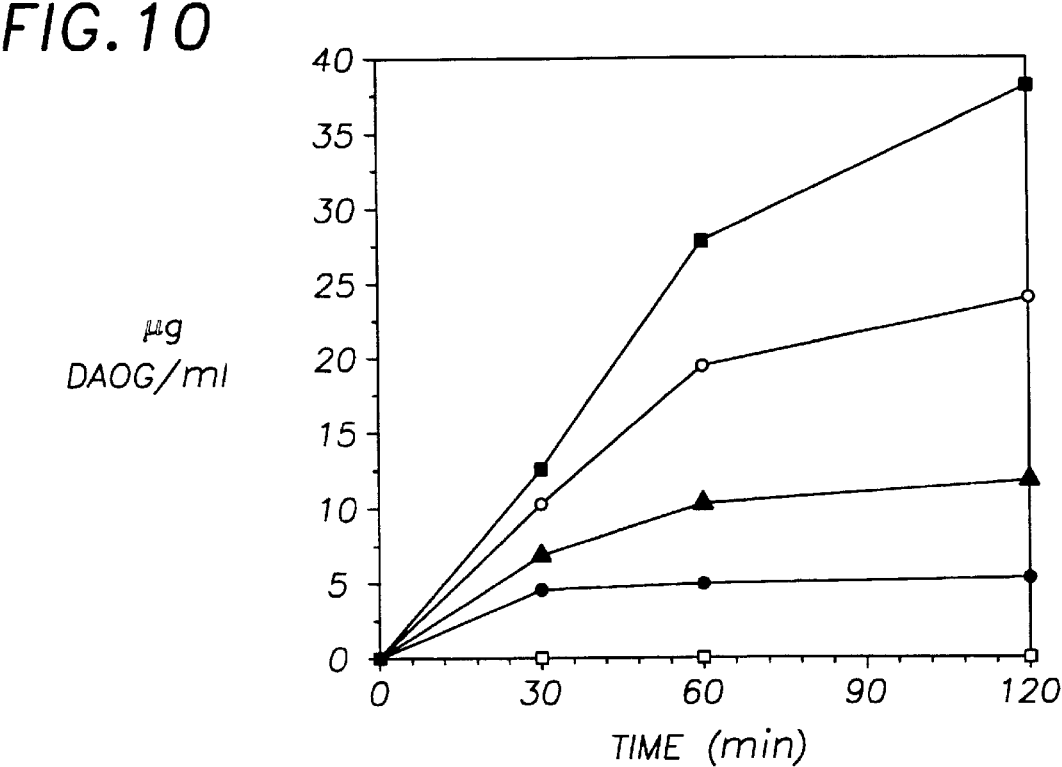
FIG. 10 shows the effect of cell-free extract protein concentration on penicillin G ring expansion by cell-free extracts. The reactions contained 50 mM Tris-HCl pH 7.4, 8 mM KCl, 8 mM $MgSO_4$, 4 mM ascorbic acid, 1.8 mM $FeSO_4$, 1.28 mM α-ketoglutarate, a4 mM DDT and 2 mg/ml penicillin G. Protein concentration was 0.2 mg/ml (□), 1 mg/ml (●), 2 mg/ml (▲), 4 mg/ml (○), or 6 mg/ml (■). Samples were taken at 2 hour and centrifuged at 14K×g rpm for 5 minutes. 200 µl of the supernatant were used in the bioassay.

Penicillin G ring expansion by cell-free extracts: Having defined successful reaction conditions for penicillin G expansion by resting cells, we tested the same conditions using cell-free extracts. As shown in FIG. 10, cell-free extracts were active under these conditions, and higher protein concentration in the reactions gave more DAOG production.

Figure 11:
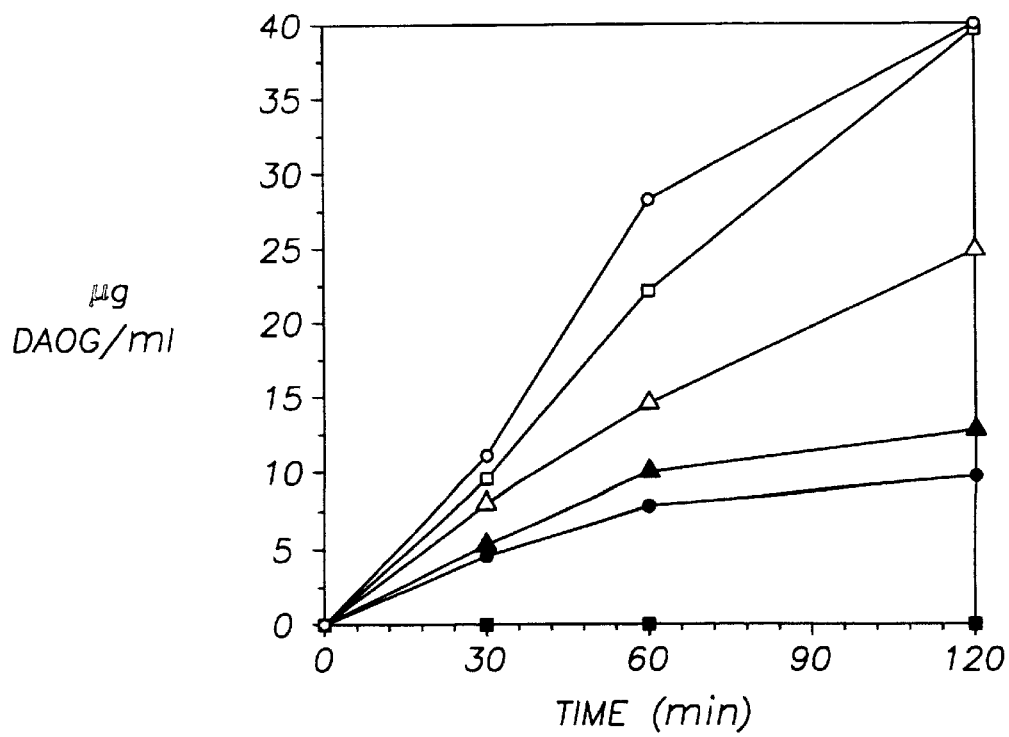
FIG. 11 shows the effect of penicillin G concentration on penicillin G ring expansion by cell-free extracts. The reactions contained 50 mM Tris-HCl pH 7.4, 8 mM KCl, 8 mM $MgSO_4$, 4 mM ascorbic acid, 1.8 mM $FeSO_4$, 14 mM DDT, and 1.28 mM α-ketoglutarate. (■) No penicillin G; (●), 0.5 mg/ml; (▲), 1 mg/ml; (Δ) 2 mg/ml; (□) 4 mg/ml; (○) 5 mg/ml. Samples were taken at 2 hour and centrifuged at 14K×g for 5 minutes. 200 µl were used in the bioassay.

We explored the effect of substrate (i.e., penicillin G) concentration on the cell-free extract reaction and found increased substrate concentration gave increased product formation (FIG. 11). We used substrate concentrations up to 15 times higher than those previously used by Maeda et al. in their attempts to expand penicillin G.

We varied the concentrations of cell-free protein, penicillin G, $FeSO_4$, and α-ketoglutarate in our cell-free reactions and found that, consistent with our above results, higher concentrations (within the limits that we tested) tended to yield more product (Table 3).

TABLE 3

Effect of Modifications in Concentration of Cell-free protein, $Fe^{2+}$, α-Ketoglutarate, and Penicillin G on Penicillin G Ring Expansion by Cell-free Extracts

| Protein (mg/ml) | $FeSO_4$ (mM) | α-ketoglutarate (mM) | Penicillin G (mg/ml) | DAOG (μg/ml) |
|---|---|---|---|---|
| 4 | 0.036 | 0.64 | 1 | 3.4 |
| 4 | 0.036 | 0.64 | 0.3 | 2.6 |
| 4 | 0.036 | 0.64 | 0.1 | 2.3 |
| 2 | 0.036 | 0.64 | 1 | 2.6 |
| 2 | 0.036 | 0.64 | 0.3 | 2.1 |
| 2 | 0.036 | 0.64 | 0.1 | <2 |
| 1 | 0.036 | 0.64 | 1 | 2.1 |
| 1 | 0.036 | 0.64 | 0.3 | <2 |
| 1 | 0.036 | 0.64 | 0.1 | <2 |
| 4 | 1.8 | 1.28 | 1 | 5.6 |
| 4 | 1.8 | 1.28 | 0.3 | 3.4 |
| 4 | 1.8 | 1.28 | 0.1 | 2.8 |

TABLE 3-continued

Effect of Modifications in Concentration of Cell-free protein, $Fe^{2+}$, α-Ketoglutarate, and Penicillin G on Penicillin G Ring Expansion by Cell-free Extracts

| Protein (mg/ml) | $FeSO_4$ (mM) | α-ketoglutarate (mM) | Penicillin G (mg/ml) | DAOG (μg/ml) |
|---|---|---|---|---|
| 2 | 1.8 | 1.28 | 1 | 3.4 |
| 2 | 1.8 | 1.28 | 0.3 | 2.3 |
| 2 | 1.8 | 1.28 | 0.1 | 2.1 |
| 1 | 1.8 | 1.28 | 1 | 2.1 |
| 1 | 1.8 | 1.28 | 0.3 | <2 |
| 1 | 1.8 | 1.28 | 0.1 | <2 |

Ring Expansion of Other Penicillins by Cell-free Extracts: We tested our reaction conditions for their ability to support ring expansion on other penicillin substrates and found detectable expansion with each of the 15 substrates that we tested. Large zones of inhibition were observed for penicillin G, penicillin X, penicillin mX, and 2-thiophenylacetyl-6-APA; intermediate size zones were observed for adipyl-6-APA, ampicillin, butyryl-6-APA, heptanoyl-6-APA, hexanoyl-6-APA, octanoyl-6-APA, penicillin F, and valeryl-6-APA; smaller zones were observed for decanoyl-6-APA, nonanoyl-6-APA, and penicillin V (Table 4). The reactions contained 4 mg/ml extract (protein concentration), 50 mM Tris-HCl pH 7.4, 1.8 mM $FeSO_4$, 1.28 mM α-ketoglutarate, 8 mM $MgSO_4$, 8 mM KCl, 4 mM ascorbic acid, 14 mM DTT, and 2 mg/ml substrate (except for penicillin mX and octanoyl-6-APA, which were used at 3 mg/ml). Samples were centrifuged at 12K rpm for 5 minutes after 2 hours of reaction. 250 μl of reaction mixture was used in each bioassay.

TABLE 4

Expansion of Penicillins Using Cell-Free *S. clavuligerus* Expandase Extracts

| Substrate | Inhibition Zone Diameter (mm) |
|---|---|
| None | 0 |
| Adipyl-6-APA | 20 |
| Ampicillin | 17 |
| Butyryl-6-APA | 17.5 |
| Decanoyl-6-APA | 7 |
| Heptanoyl-6-APA | 16.5 |
| Hexanoyl-6-APA | 19.5 |
| Nonanoyl-6-APA | 10.5 |
| Octanoyl-6-APA | 16 |
| Penicillin F | 21 |
| Penicillin G | 29 |
| Penicillin V | 7.5 |
| Penicillin mX | 30.5 |
| Penicillin X | 30.5 |
| 2-Thiophenylacetyl-6-APA | 32 |
| Valeryl-6-APA | 15 |

Example 2

Conversion of Penicillin G into DAOG by Growing Cells of *S. clavuligerus* NP1

Materials and Methods

Microorganisms: For expandase production, we utilized the NP1 mutant described in Example 1. For our bioassay, we utilized *E. coli* strain ESS, a mutant that is hypersensitive to β-lactam antibiotics.

Media: Seed culture was prepared using 250 ml baffled flasks containing 40 ml MST medium (90 mM MOPS, 3%

Trypticase Soy Broth without Dextrose, 1% soluble starch) adjusted to pH 7.0 before autoclaving. Fermentation was carried out in the same medium or in the defined medium described by Mahro and Demain (1987) containing, per liter, 5 g MOPS; 3.5 g $K_2$ $HPO_4$; 1 ml trace solution containing 1 mg $FeSO_4.7H_2O$, 1 mg, $MnCl_2.4H_2O$, 1 mg $ZnSO_4.H_2O$ and 1 mg $CaCl_2$; 2 g L-asparagine; 0.6 g $MgSO_4.7H_2O$; 10 g glycerol; initial pH 7.0.

Culture Conditions: For the seed culture, each flask was inoculated with 50 µl of a spore suspension (prepared and stored in 20% glycerol at −80° C.) and incubated at 30° C. for 48 h. Fermentation were conducted in 250 ml baffled flasks containing 30 ml of medium at 30° C. at 250 rpm. Fermentations were started by transferring 1.5 ml of unwashed mycelium from the seed culture and their duration was 5 days. Once a day, samples were taken for pH, biomass and antibiotic analyses. Growth was measured as dry cell weight.

Bioassay: Cephalosporin type antibiotic(s) were detected by bioassay using *Escherichia coli* Ess seeded in LB (1% Tryptone, 0.5% NaCl, 0.5% Yeast Extract, 0.1% Glucose) 0.8% agar medium in the presence of penicillinase (Difco Laboratories, Detroit, Mich.). This is a narrow spectrum β-lactamase that destroys all kinds of penicillins but not cephalosporins. Assays were conducted with filter paper discs saturated with 100 µl of standard (deacetoxycephalosporin G) or supernatants from the fermentation flask. The diameters of zones of growth inhibition were measured after overnight incubation at 37° C.

HPLC Analysis: We were interested in identifying which cephalosporin(s) was produced by growing cells. For that purpose, we developed a rapid system for the separation of penicillin G and deacetoxycephalosporin G using HPLC. The equipment consisted of a Waters LC Module I, 486M1 detector and W600 pump, and a µBondapack C18 column (30 cm×3.9 mm). The mobile phase was 10 mM $KH_2PO_4$ (adjusted to pH 3 with concentrated phosphoric acid)-methanol (60:40 v/v). Samples (20 µl) of the fermentation broths were analyzed at a flow rate of 1 ml/min with detection at 225 nm.

Results

We found that growing *S. clavuligerus* NP1 cells converted penicillin G to DAOG. Specifically, cells grown in the absence of added penicillin G produced only very low levels (in MST medium) of cephalosporin, or no detectable cephalosporin at all (defined medium). Cells grown in the presence of penicillin G produced strong zones of inhibition. In MST supplemented with 50 µg penicillin G/ml, approximately 21% conversion (i.e., 10.5 µg cephalosporin/ml) was observed after 72 hours of incubation; in MST supplemented with 100 µg penicillin G/ml, the same level of conversion was observed after 96 hours. In defined medium, the conversion rates were 9.1% (4.55 µg cephalosporin/ml) for 50 µg/ml penicillin G and 10.5% (10.5 µg cephalosporin/ml) for 100 µg/ml penicillin G after 48 hours.

When the extracellular culture fluids were analyzed by HPLC, a penicillin G peak (observed at 0 h of growth to be eluting with a retention time of 5.6 min) decreased markedly over the 24–120 h time period, and a new peak, corresponding to DAOG and eluting at 4.6 min, appeared. Two additional peaks of unknown origin, having retention times shorter than 4.6 min, were also observed as the reaction progressed.

Example 3

Effect of Alcohols on Penicillin G Conversion by Resting *S. clavuligerus* NP1 Cells Materials and Methods Microorganisms, Media, and Culture Conditions: All experiments were done using *S. clavuligerus* NP1. Seed cultures were developed using 250 ml baffled flasks containing 40 ml of MST medium: 1% soluble starch (Sigma Chemical Co., St. Louis, Mo.); 3% Trypticase Soy Broth Without Dextrose (BBL, Cockeysville, Md.); 90 mM MOPS buffer, pH adjusted to 7.0 before autoclaving. Each flask was inoculated with 50 µl of a spore suspension (stored in 20% glycerol at −80° C.) and incubated at 30° C., 250 rpm for 48 h.

From a seed culture, 4 ml were transferred to 500 ml baffled flasks containing 80 ml of MT medium (3% Trypticase Soy Broth Without Dextrose; 90 mM MOPS buffer, pH adjusted to 7.0 before autoclaving) with or without 1–2% ethanol or methanol. Alcohols were added just before inoculation. Cells were grown at 30° C., 250 rpm for 24 h. Mycelia from each flask were washed twice and, finally, resuspended in 10 ml of distilled water. Four ml of this cell suspension were used in the ring-expanding biotransformation.

Ring Expansion: The ring expansion mixture contained 1.8 mM $FeSO_4$, 1.28 mM α-ketoglutarate, 4 ml cell suspension, 5.6 mM penicillin G and 50 mM MOPS (pH 6.5) in a final volume of 10 ml contained in 250 ml baffled Erlenmeyer flasks. Additions were made in the order established by Shen et al. (Shen et al., *Enzyme Microb. Technol.* 17:231–234, 1984). Incubation was at 220 rpm and 30° C. for 1 to 3 h. Samples were collected and centrifuged. Biotransformation activity was detected by paper disc-agar diffusion bioassay.

Detection of Expandase Activity: Expandase activity was detected by paper disc-agar diffusion bioassay. Two superimposed paper discs (¼ inch; Schleicher & Schuell, Keene, N.H.) were saturated with 100 µl of each supernatant or standard. After each application, the discs were allowed to dry for 30 min in a laminar hood and then placed on Petri plates containing 10 ml of LB (1% tryptone, 0.5% NaCl, 0.5% yeast extract, 0.1% glucose) 0.8% agar medium containing 50,000 IU/ml of penicillinase (Difco Bacto penase concentrate, Difco Laboratories, Detroit, Mich.) seeded with *E. coli* ESS (a β-lactam-supersensitive mutant). The plates were incubated overnight at 37° C. The penicillinase used is a narrow spectrum β-lactamase that destroys the substrate penicillin G but not cephalosporins. The diameters of zones of growth inhibition were measured and quantified with calibration curves using pure DAOG as standard.

HPLC Analysis: The equipment used for HPLC consisted of a Waters LC Module I with a 486M1 detector, W600 pump and a µBondapack C18 column (30 cm×3.9 mm) (Waters Associates, Milford, Mass.). Samples (20 µl) from the biotransformation mixtures were analyzed at a flow rate of 1 ml/min with detection at 260 nm. The elution was done with 10 mM $KH_2PO_4$ (adjusted to pH 3 with concentrated phosphoric acid)-methanol (80:20 v/v) in the isocratic mode during the first 5 min followed by a 15 mn linear gradient from 100% of the initial solvent ($KH_2PO_4$-methanol) to 100% methanol.

Dry Cell Weight (DCW) Assay: Two samples of 1 ml were taken from each cell suspension prepared in distilled water (10 ml), centrifuged (14,000×g, 10 min) and dried to constant weight at 65° C. The weights listed are those in the reaction mixture.

Preparation of DAG: DAG was provided by Saul Wolfe, who prepared it as follows: A solution of 7-aminodeacetylcephalosporanic acid (801 mg, 3.48 mmoles) and sodium bicarbonate (980 mg, 11.7 mmoles), in acetone (26 ml) and water (32 ml), was treated during 10 min at 0° C. with a solution of phenylacetyl chloride (530 µl, 620 mg. 4.01 mmoles) in acetone (3.2 ml). The reaction mixture was stirred for 1.5 h, diluted with ethyl acetate (2×20 ml) and the phases were separated. The organic layer was discarded, and the aqueous layer was acidified to pH 3–4 using 1 M hydrochloric acid and then extracted with ethyl acetate (2×20 ml). This extract was washed with saturated sodium chloride (40 ml), dried over anhydrous magnesium sulfate, and evaporated to give a white solid. This solid was triturated with diethyl ether, cooled to −20° C., and filtered to give the product (643 mg, 53%).

$^1$HMR (acetone-d6, δ): 7.98 (1H, d, 8.7 Hz, NH), 7.34 (4H, t. Ar), 7.24 (1H, d, Ar), 5.78 (1H, dd, 4.8, 8.7 Hz, β-lactam CH), 4.43 (1H, d, 13.5 Hz, PhCHH), 4.36 (1H, d, 13.5 Hz, PhCHH), 3.67 (1H, d, 14.3 Hz, SCHH), 3.62 (1H, d, 14.3 Hz, SCHH), 3.68 (1H, d, 18.4 Hz, CHHOH), 3.61 (1H, d, 18.4 Hz, CHHOH). IR (Kbr): 3401, 3237, 1765, 1723, 1649 cm$^{-1}$.

Calcd. for $C_{16}H_{16}N_2O_5S \cdot 0.25H_2O$: C, 54.46; H, 4.71; N, 7.94 Found: C, 54.90; H, 4.89; N, 7.76.

Results

We found that specific conversion of penicillin G to DAOG by growing *S. clavuligerus* cells could be stimulated by exposing the cells to stress in the form of alcohol added to the growth medium. We used specific production as a measure of conversion in these experiments rather than volumetric production in order to normalize the effect of inhibition of *S. clavuligerus* growth by the alcohol. As shown in Table 5, after 3 hours of reaction, cells that had been grown in MST medium produced the lowest specific amount of cephalosporins; cells that had been grown in MT medium (identical to MST medium except that MT medium lacks starch) produced moderately more, and cells that had been grown on MT medium supplemented with 1% ethanol or 2% ethanol produced substantially (up to 6- to 7-fold) more. A modest increase in production was also observed with cells that had been grown on MT medium supplemented with 1% methanol.

TABLE 5

Effect of Growth on Alcohol for Penicillin G Ring Expansion by Resting Cells

| Medium | DCW (mg/ml) | Cephalosporin Production | |
|---|---|---|---|
| | | Volumetric (μg/ml) | Specific (μg/mg) |
| MST | 5.8 | 5.8 | 1.0 |
| MT | 3.6 | 5.3 | 1.5 |
| MT + 1% E | 3.4 | 12.3 | 3.6 |
| MT + 2% E | 0.9 | 6.3 | 7.0 |
| MT + 1% M | 3.0 | 5.2 | 1.7 |
| MT + 2% M | 2.9 | 4.3 | 1.5 |

We noted that, if alcohol addition was delayed to later times in cell growth (2 h, 6 h, or 12 h), there was no stimulatory effect on cephalosporin production. Also, no stimulation of cephalosporin production was observed when MST medium, instead of MT medium, was supplemented with an alcohol. Indeed, addition of an alcohol to MST medium completely inhibited penicillin G expansion as detected in our assays.

We also note that supplementation with alcohol had modest negative effects on cell growth. Specifically, while cells grown in MST or MT formed typical masses of tangled hyphae, cells grown in alcohol-supplemented cultures demonstrated different morphologies. In 1% ethanol, the hyphae were more dispersed; in 2% ethanol, the hyphae were extensively fragmented and dispersed. Also, DCW assays indicated that growth was reproducibly diminished in 1% ethanol or 1–2% methanol as compared with 0% alcohol in MT; 2% ethanol severely restricted growth. Concentrations of alcohol higher than 2% completely inhibited growth.

Figure 12A:
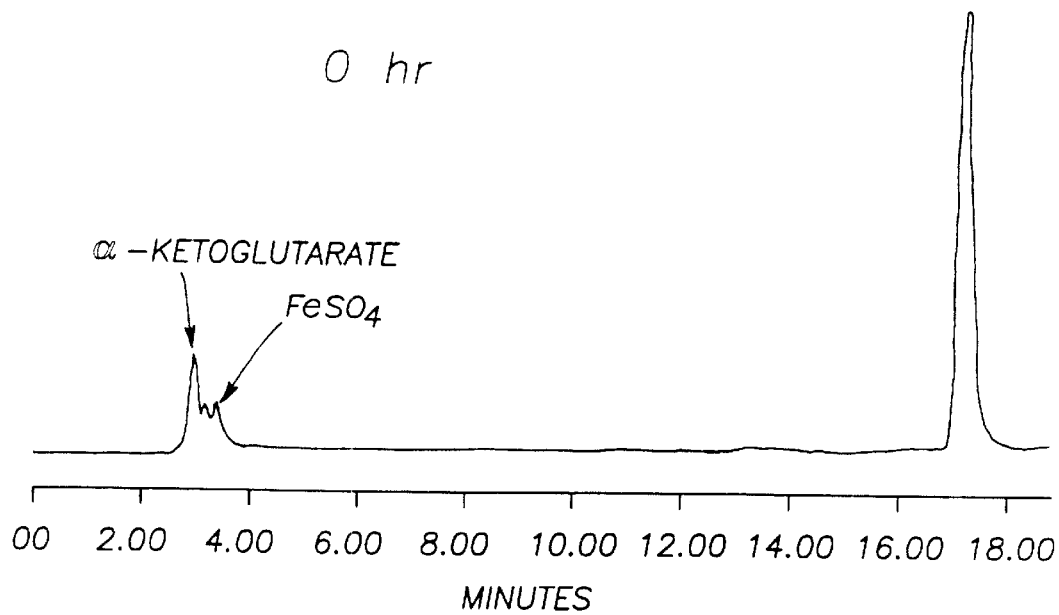
FIG. 12 shows an HPLC analysis of penicillin G ring expansion to DAOG by resting S. clavuligerus NP1 cells. Sensitivity was 0.12 absorbance units of full sensitivity (AUFS). Cells were grown in MT+1% ethanol.
Figure 12B:
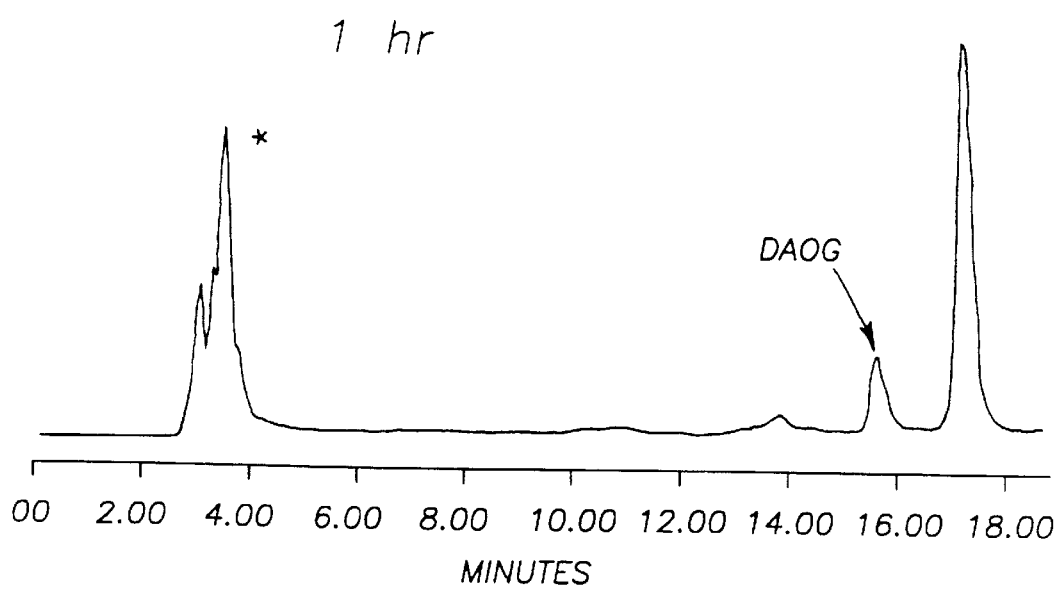
Figure 12C:
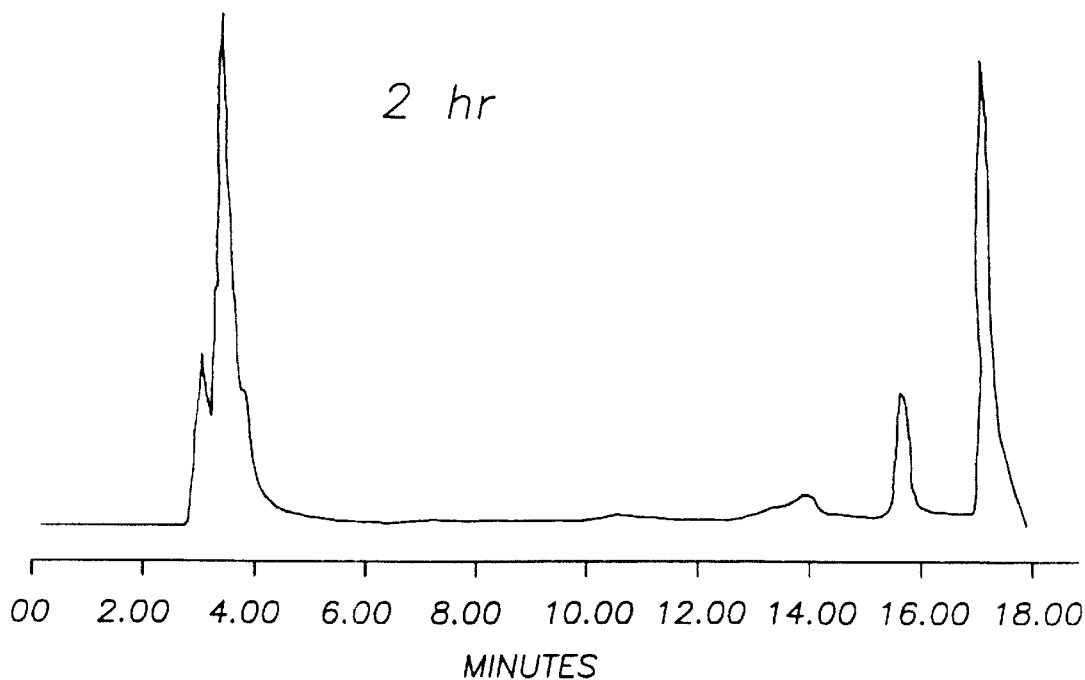
Figure 12D:
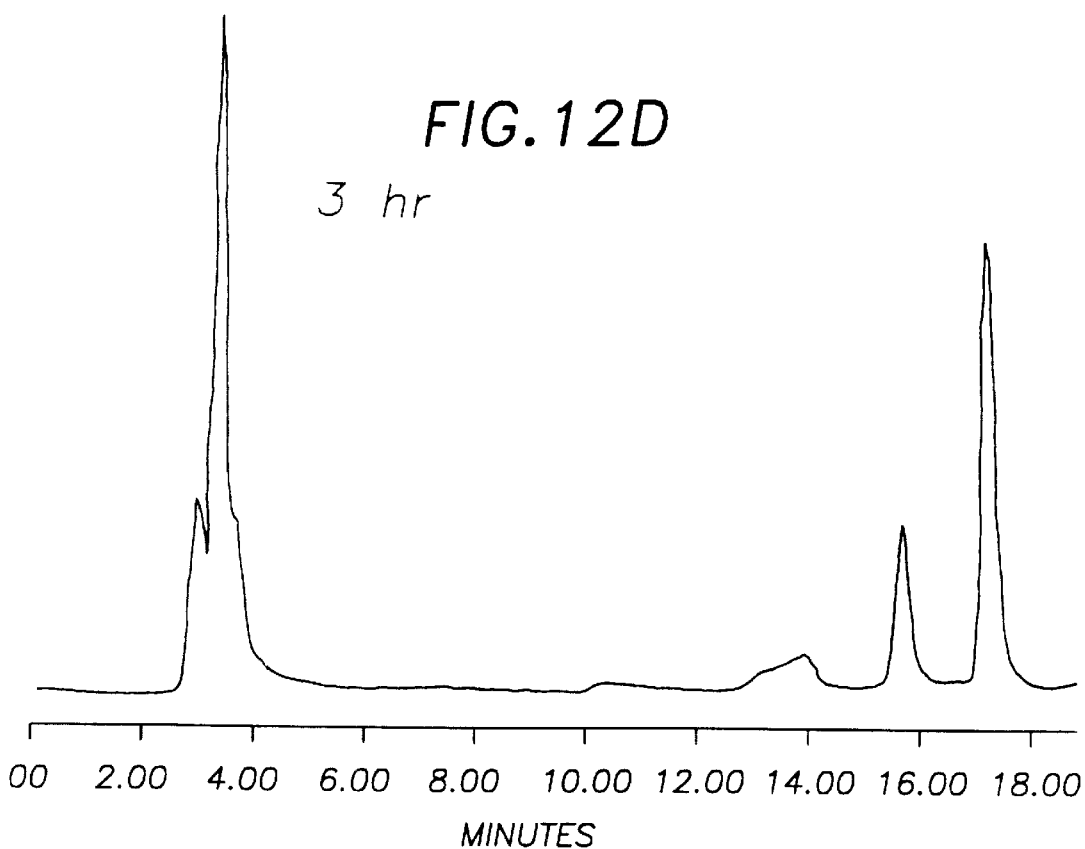

We used HPLC analysis to track the bioconversion reactions stimulated by our resting cells. Chromatograms taken before the start of the reaction (see FIG. 12A) showed peaks at 3.1, 3.6, and 17 min, corresponding to $FeSO_4$, α-ketoglutarate, and penicillin G, respectively. After 1 hour of incubation, two new peaks, at 3.65 and 15.3 mins, appeared on the chromatogram (FIG. 12B). The 15.3 min peak was DAOG but the 3.65 min peak (*) remains unidentified. During the subsequent 2 hours of incubation (FIGS. 12C and D), the 15.3 min and 3.65 min peaks increased in size. No peak corresponding to DAG was detected during the reaction; standards tested indicated that a DAG peak would have eluted at 8 min.

Example 4

Effect of Buffer Selection, Cell Treatment, and Substrate Concentration on Penicillin G

EXPANSION BY RESTING *S. CLAVULIGERUS* NP1 CELLS

Materials and Methods

Microorganisms, Media, and Culture Conditions: *S. clavuligerus* mutant NP-1, described in Example 1 was used for these studies. A seed culture was made by inoculating a spore suspension (40 μl) into 40 ml MST medium in 250 ml baffled flasks, and incubating for 2 days at 30° C. and 250 rpm. One ml of the seed culture was used as inoculum for the main culture which contained 80 ml of MST medium in 500 ml unbaffled flasks. The flasks were incubated for 24 h at 30° C. and 250 rpm.

Preparation of Resting Cells: Cells were harvested by centrifugation at 14,000×g, for 15 min at 4° C. and washed twice with cold deionized water. They were resuspended in 10 ml of water.

Ring Expansion Reaction: The standard reaction mixture (10 ml) contained 0.05 M Tris-HCl pH 7.4, 8.0 mM KCl, 8.0 mM $MgSO_4 \cdot 7H_2O$, 4.0 mM ascorbic acid, 1.8 mM $FeSO_4 \cdot 7H_2O$, 1.28 mM α-ketoglutaric acid, 20 mg/ml penicillin G and 4.0 ml cell suspension. The order of addition of the components were as previously described (Shen et al., *Enzyme Microb. Technol.* 6:402–404, 1984). The reaction started when penicillin G was added to the reaction mixture which was incubated at 30° C. and 220 rpm.

Expandase Assay: Product formation was estimated by the paper disk-agar diffusion bioassay as described in example 1, using deacetoxycephalosporin G as standard. *Escherichia coli* strain Ess, a β-lactam supersensitive, mutant was used as the assay microorganism.

Results

In an effort to expand the discovery reported in Example 1, we analyzed the effects of buffer selection, treatment of resting cells, substrate concentration, and cell biomass on the extent of penicillin G conversion by *S. clavuligerus* NP1 resting cells.

Figure 13:
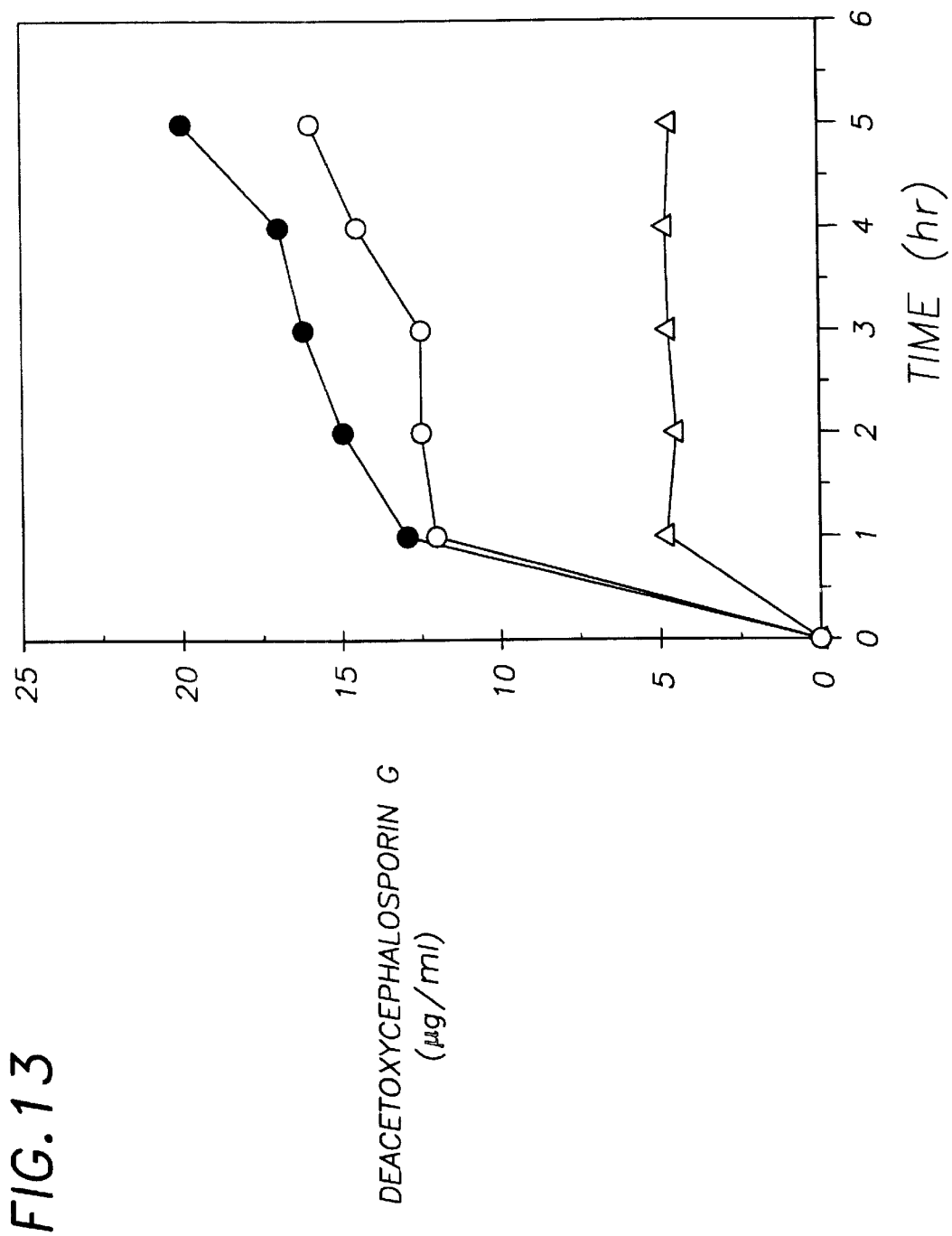
FIG. 13 shows the effect of buffer selection on penicillin G conversion by resting S. clavuligerus NP1 cells. (●) 0.05 M MOPS, pH 6.5, (○) 0.05 M HEPES, pH 6.5, (Δ) 0.05 M Tris-HCl, pH 7.4.

FIG. 13 demonstrates that the use of either 0.05 M MOPS buffer at pH 6.5 or 0.05 M HEPES buffer at pH 6.5 increases the production of cephalosporin more than two-fold as compared with reactions performed in 0.05 M Tris-HCl pH 7.4. Subsequent reactions were therefore performed in 0.05 M MOPS, pH 6.5.

FIG. 13 also demonstrates that, in all buffers, cephalosporin production proceeds rapidly for about 1 hour and then stops altogether or proceeds at a significantly reduced rate. We asked whether one of the reaction component might be inhibiting the reaction, perhaps by inactivating the expandase after the approximately 1 hour period. Specifically, we preincubated the resting cells for 3 hours in the presence of one or more of the reaction components; at the end of the preincubation period, all missing components were added.

Figure 14:
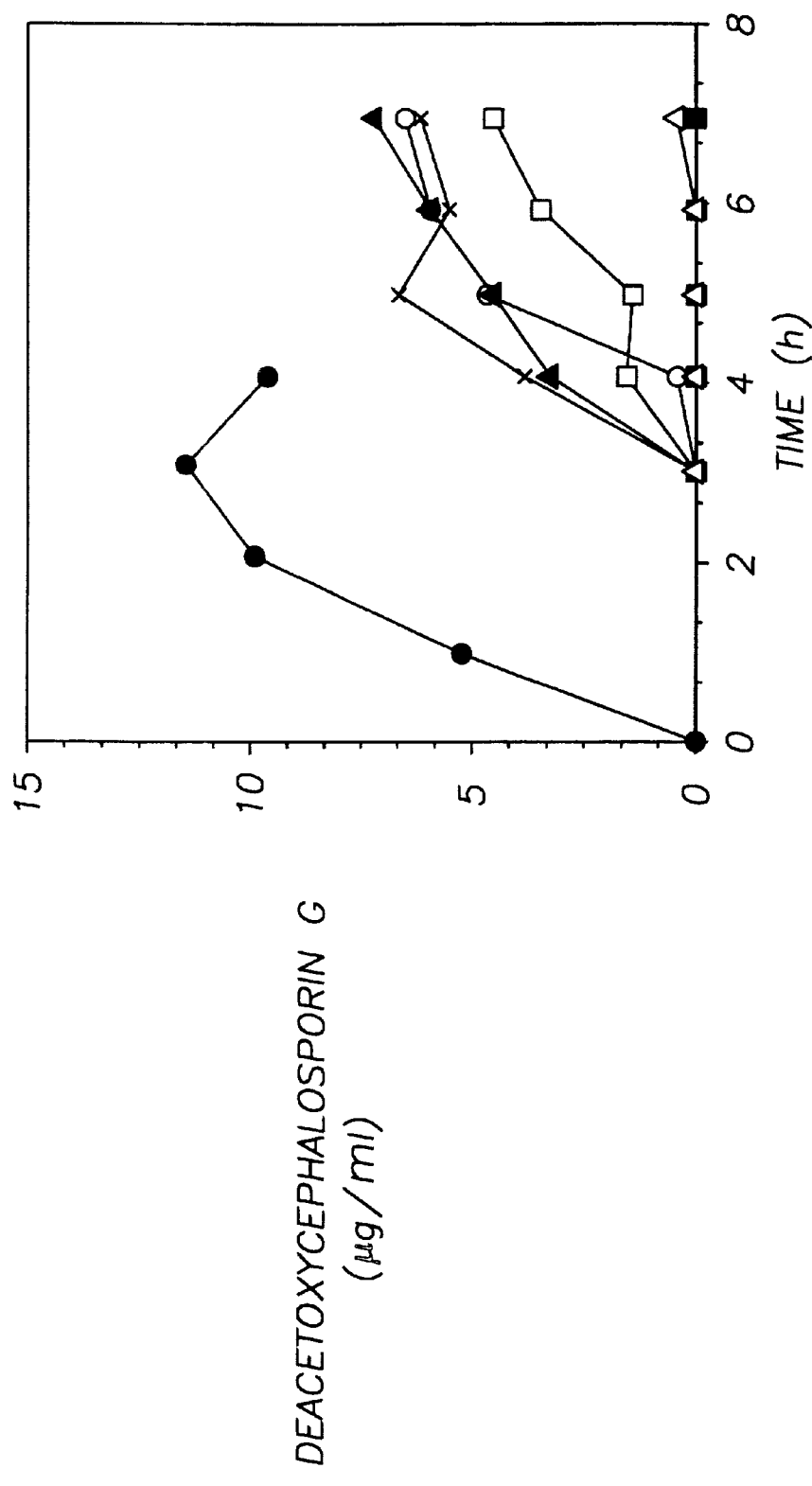
FIG. 14 shows the effect on penicillin G conversion of preincubating resting S. clavuligerus NP1 cells with one or more components of the reaction mixture prior to ring expansion. Preincubations: (●) none, (○) $Fe^{2+}$, (▲) ascorbic acid, (×) α-ketoglutarate, (■) ascorbic acid+$Fe^{2+}$, (Δ) ascorbic acid+$Fe^{2+}$+α-ketoglutarate.

FIG. 14 shows that, when cells were preincubated with either buffer, $Fe^{2+}$, ascorbic acid, or α-ketoglutarate, product formation occurred more slowly and total production was reduced by about 50%. Preincubation with a combination of $Fe^{2+}$ and ascorbic acid, with or without α-ketoglutarate, virtually eliminated all penicillin G conversion. These experiments demonstrate that the flattening of the product formation curve over time is most likely due to enzyme destruction by $Fe^{2+}$ in combination with ascorbate and/or α-ketoglutarate.

Figure 15:
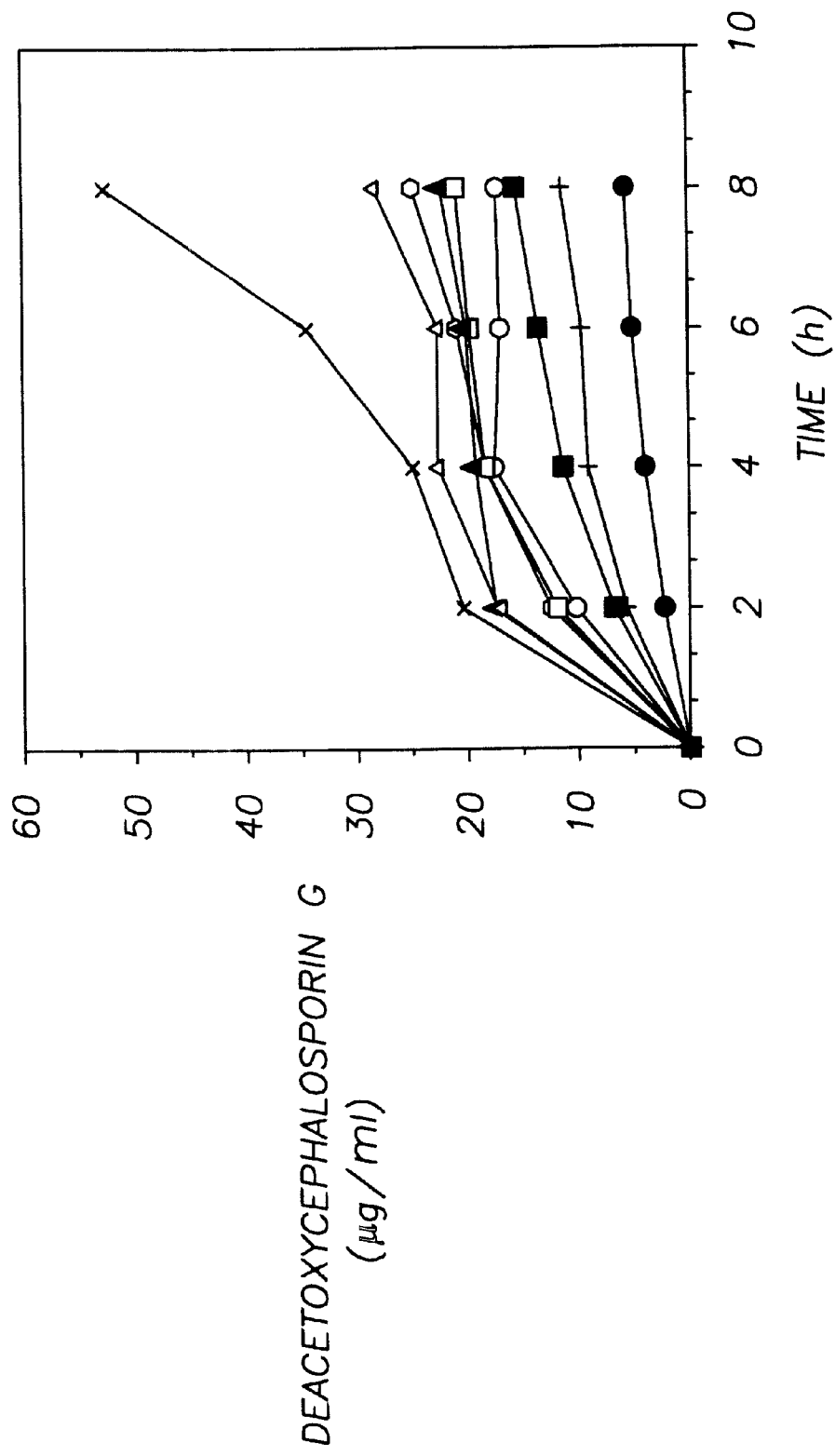
FIG. 15 shows the effect of substrate concentration on product formation by resting cells. Substrate was present at: (●) 0.063 mg/ml, (+) 0.125 mg/ml, (■) 0.25 mg/ml, (○) 0.5 mg/ml, (▲) 1.0 mg/ml, (□) 2.0 mg/ml, ( ) 4.0 mg/ml, (Δ) 6.0 mg/ml, and (×) 8.0 mg/ml.
Figure 16:
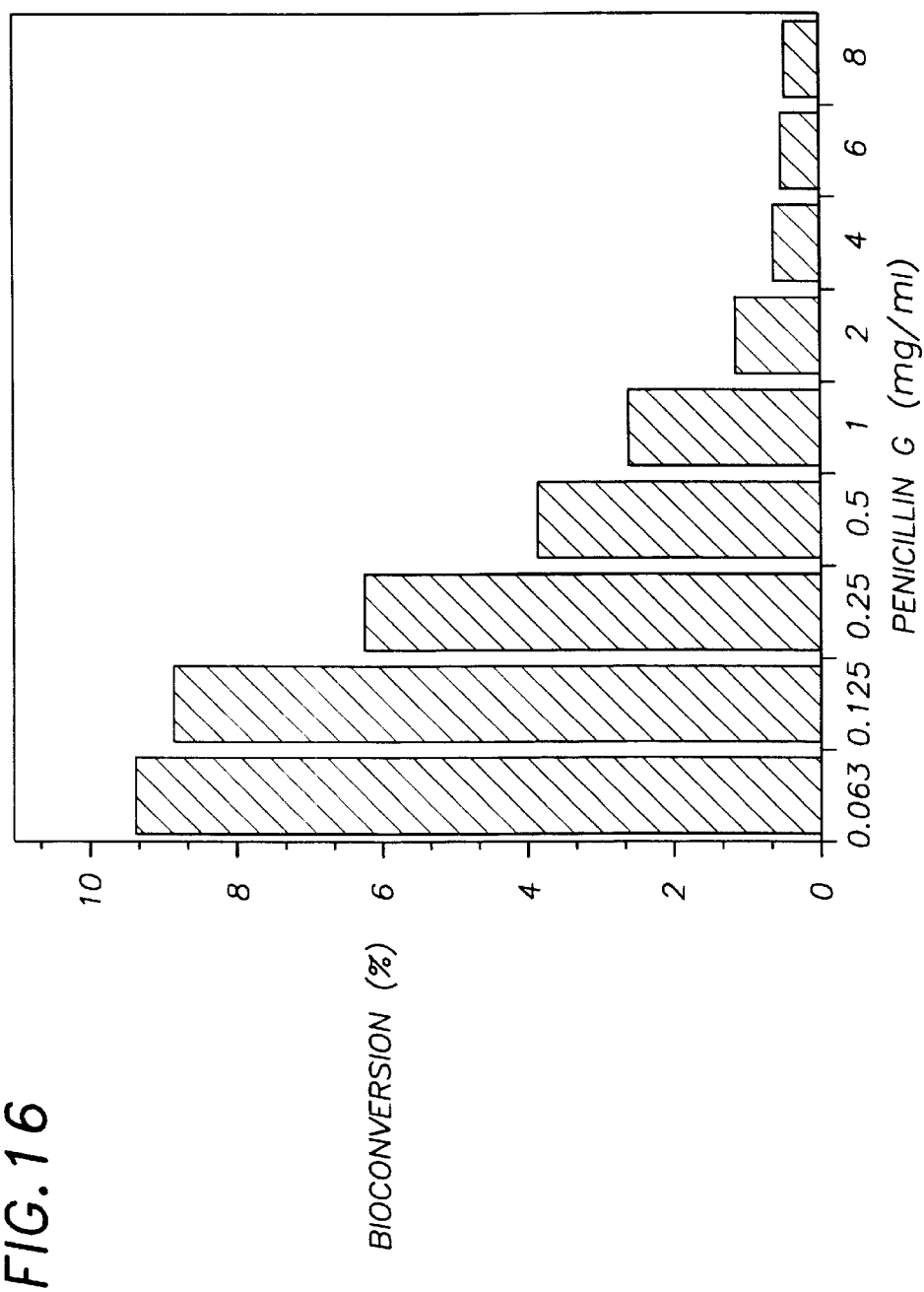
FIG. 16 shows yields of penicillin G conversion by resting S. clavuligerus NP1 cells, based on amount of substrate changed, at different concentrations of penicillin G.

In addition to testing the effects of buffer selection and component preincubation on the penicillin G conversion reaction, we tested the effect of increases or decreases in substrate concentration. As shown in FIGS. 15 and 16, larger amounts of product were produced when more substrate was added (FIG. 15), but the percent conversion was dramatically reduced (FIG. 16). Specifically, at 8 mg/ml of penicillin G, about 0.4% was converted; at 2 mg/ml, about 1.0% was converted, and at 0.063 mg/ml, about 9.0% was converted. Subsequent experiments revealed conversions as high as 16.5% for 0.015 mg/ml substrate.

Figure 17:
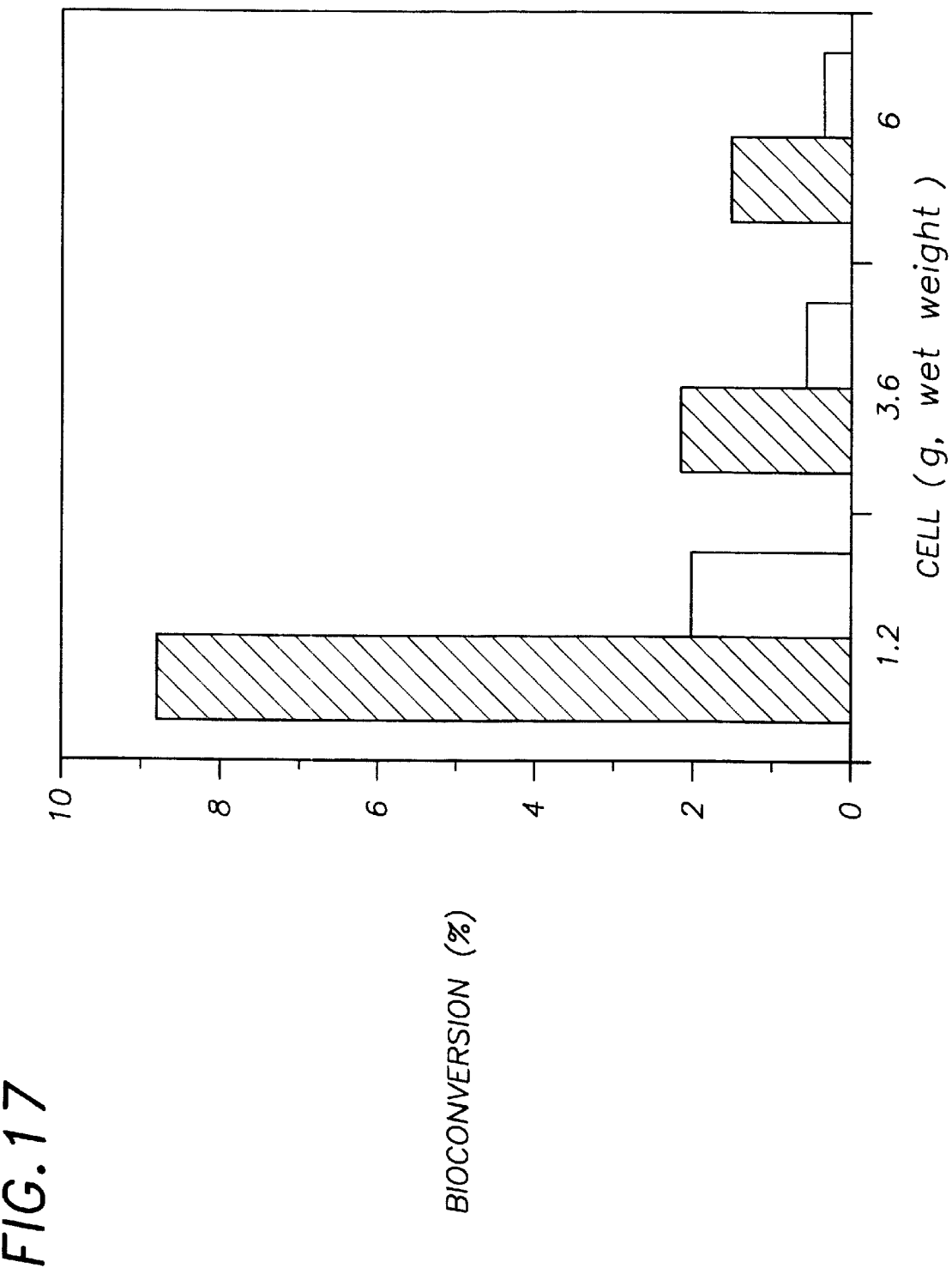
FIG. 17 shows the effect on penicillin G conversion yields of different biomass levels of resting cells (gram wet weight in 10 ml of reaction mixture) at two different concentrations, 0.063 mg/ml (■) and 2 mg/ml (□), of penicillin G.

Finally, we tested the effects on percent conversion of increasing the concentration of biomass in our resting cell reactions. As is shown in FIG. 17, we found that, for two different concentrations of penicillin G (0.063 mg/ml and 2 mg/ml), conversion was markedly enhanced at lower cell concentrations.

Example 5

Conversion of Penicillin G to DAOG by Immobilized *S. clavuligerus* NP1 Cells

Materials and Methods

Culture Conditions: A seed culture of *S. clavuligerus* mutant NP-1 was made by thawing a frozen preparation of spores and inoculating 40µl into 40 ml MST medium containing 90 mM MOPS buffer, pH 7.0, 1% starch and 3% trypticase soy broth medium without dextrose (BBL Becton Dickinson Microbiology Systems, Cockeysville, Md.) in 250 ml baffled flasks. The flasks were incubated for 2 days at 30° C. and 250 rpm. One ml of the seed culture was used as inoculum for the main culture which contained 80 ml of MST medium in 500 ml unbaffled flasks. The flasks were incubated for 24 h at 30° C. and 250 rpm.

Preparation of Resting Cells: Cells were harvested by centrifugation at 14,000×g for 15 min at 4° C. and washed twice with cold deionized water. Washed cells were resuspended in 10 ml of water giving a concentration (wet weight) of about 0.31 g/ml.

Preparation of Polyethyleneimine (PEI)-Barium Alginate Entrapped Cells: Resting cells from a one-day old culture of *S. clavuligerus* NP-1 (2 g wet weight) were directly resuspended in 20 ml of 1.5% (w/v) sodium alginate solution. The resulting sodium alginate-cell suspension was placed into a 10 ml plastic syringe containing a 26.6 G needle. The suspension was added drop by drop into a slowly stirring hardening solution of 2% (w/v) barium chloride containing 1% (w/v) PEI, giving beads of about 1.5–2.0 mm in diameter. The beads were filtered on a plastic net, washed twice with water and suspended in 0.05M MOPS buffer, pH 6.5 and stored at 4° C. until used.

Ring Expansion Reaction: The standard reaction mixture (10 ml) contained 0.05 M Tris-HCl buffer (pH 7.4), 8.0 mM KCl, 8.0 mM $MgSO_4.7H_2O$, 4.0 mM ascorbic acid, 1.8 mM $FeSO_4.7H_2O$, 1.28 mM α-ketoglutaric acid, 200 mg penicillin G and 4.0 ml of free cell suspension, or 3.4 g (wet weight) of cells in barium alginate beads. The order of addition of the components were as described (Shen et al., *Enzyme Microb. Technol.* 6:402–404, 1984). The reaction started when penicillin G was added to the reaction mixture and was incubated at 30° C. and 220 rpm for 1–12 h. Product formation was estimated by the paper disk-agar diffusion bioassay using deacetoxycephalosporin G as standard and penicillinase to destroy the substrate penicillin G. *Escherichia coli* Ess, a β-lactam supersensitive mutant, was used as assay microorganism.

Expandase Assay: Product formation was estimated by the paper disk-agar diffusion bioassay using deacetoxycephalosporin G as standard and penicillinase to destroy the substrate penicillin G. *Escherichia coli* Ess (Kohsaka et al., *Biochem. Biophys. Res. Commun.* 70:465–573, 1976), a β-lactam supersensitive mutant, was used as assay microorganism.

Materials: Alginic acid sodium salt was from Aldrich Chemical Company, Inc., Milwaukee, Wis., Agarose Type VII low gelling temperature, polyethyleneimine 50% (PEI), penicillin G, ascorbic acid and α-ketoglutaric acid were from Sigma Chemical Company (St. Louis, Mo.). Deacetoxycephalosporin G was a gift from Antibiotics, S.A. (León, Spain) and Bactopenase was from Difco Laboratories (Detroit, Mich.).

Results

Figure 18:
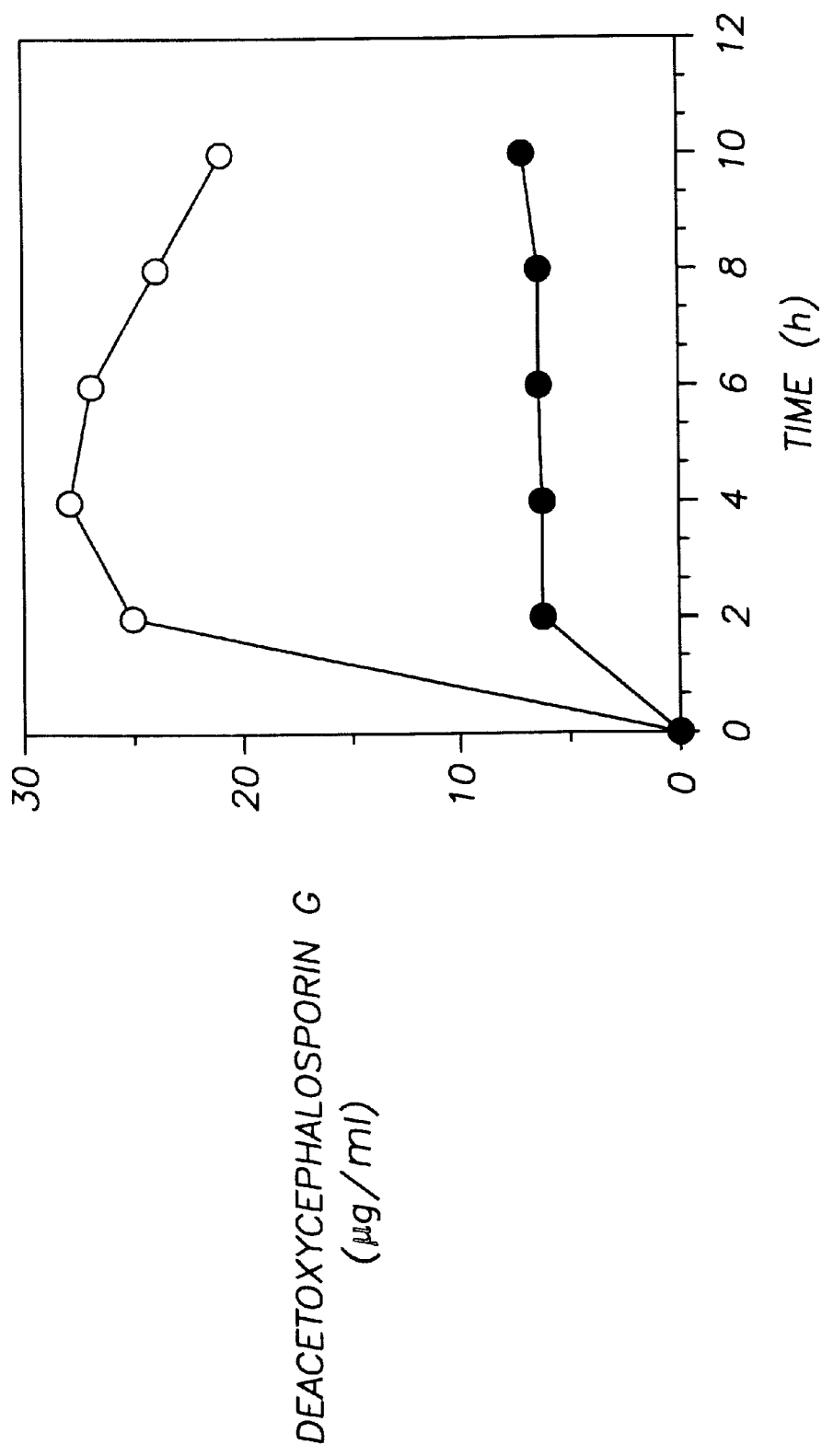
FIG. 18 compares the penicillin G expansion activity of S. clavuligerus NP1 resting cells entrapped in PEI-barium alginate (●) as compared with free resting cells (○).

This Example demonstrates that *S. clavuligerus* NP1 cells immobilized by entrapment on a polymeric matrix are able to perform oxidative ring expansion of penicillin G into DAOG. Specifically, resting cells entrapped in PEI-barium alginate (1.5%) were shown to be able to expand penicillin G (FIG. 18). Because the weights of entrapped resting cells could not be normalized to those of free resting cells, the curves presented in FIG. 18 cannot be directly compared to one another. However, we find that increases in entrapped biomass concentration resulted in increased product formation (FIG. 19).

Figure 19:
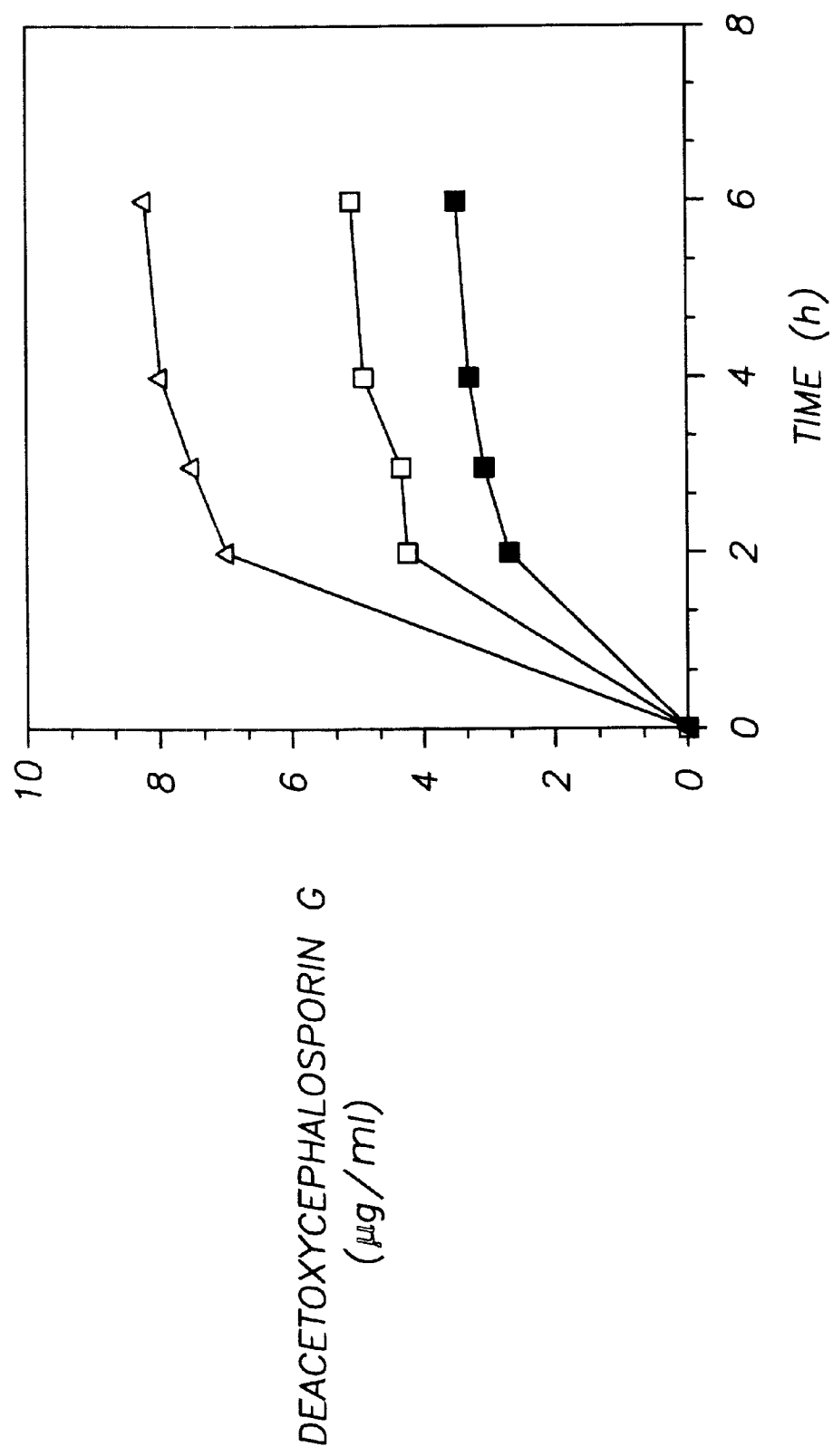
FIG. 19 shows the effect of biomass concentration on penicillin G conversion activity of entrapped S. clavuligerus NP1 cells. A constant amount of beads (3.4 g wet weight/10 ml reaction mixture) was used. (■) 2 g cells (wet weight), (□) 4 g cells, (▲) 6 g cells.
Figure 20A:
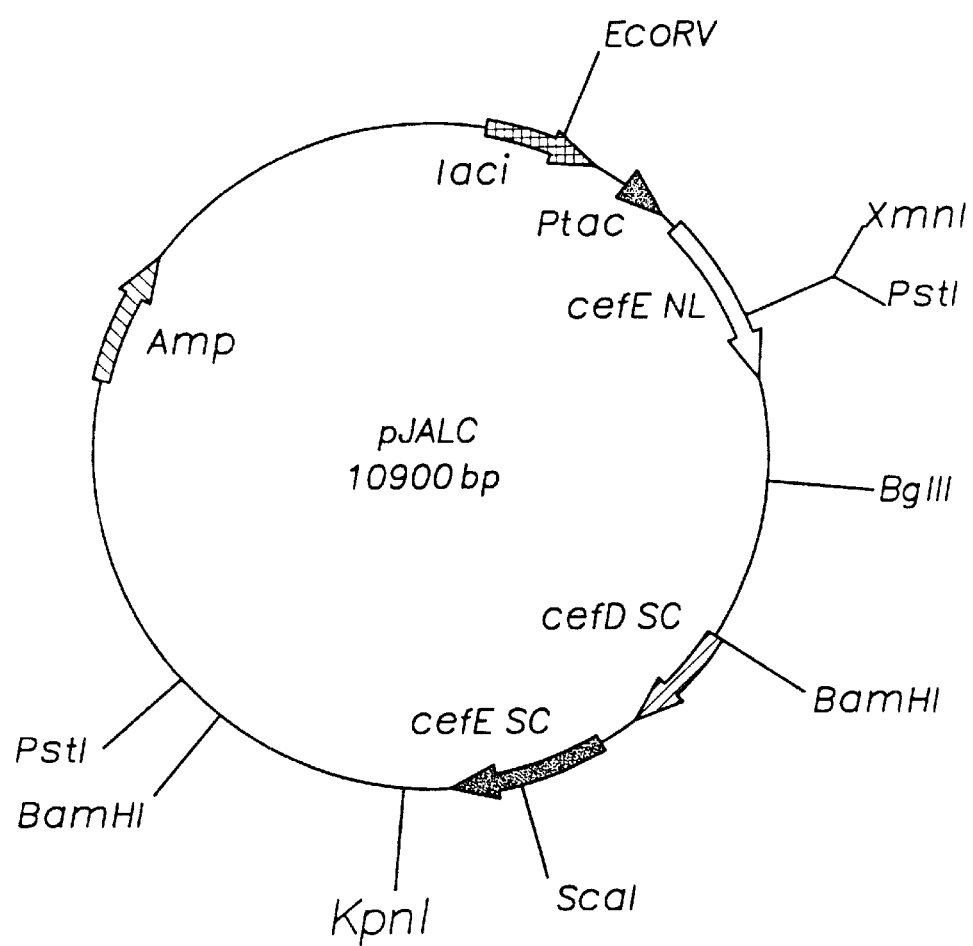
FIG. 20 shows plasmids utilized to study homologous recombination.
Figure 20B:
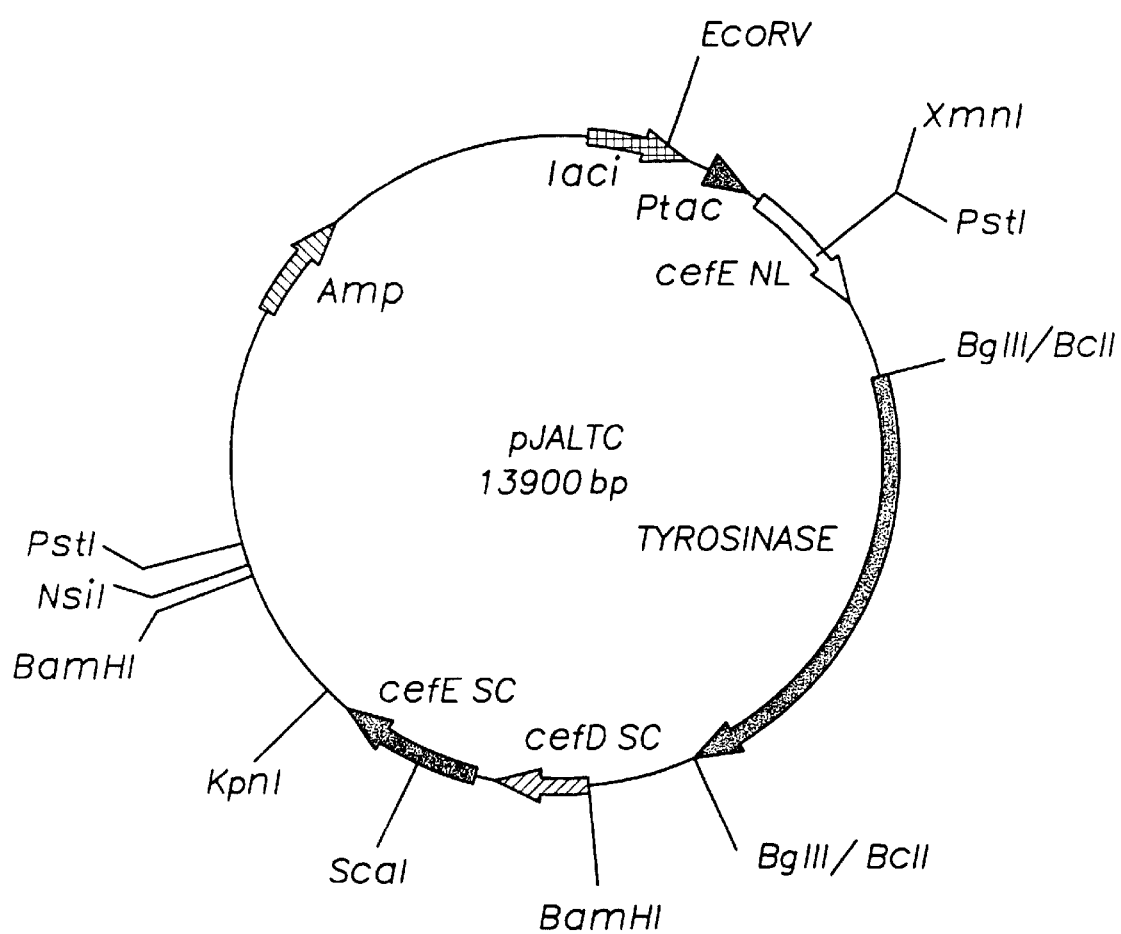
Figure 20C:
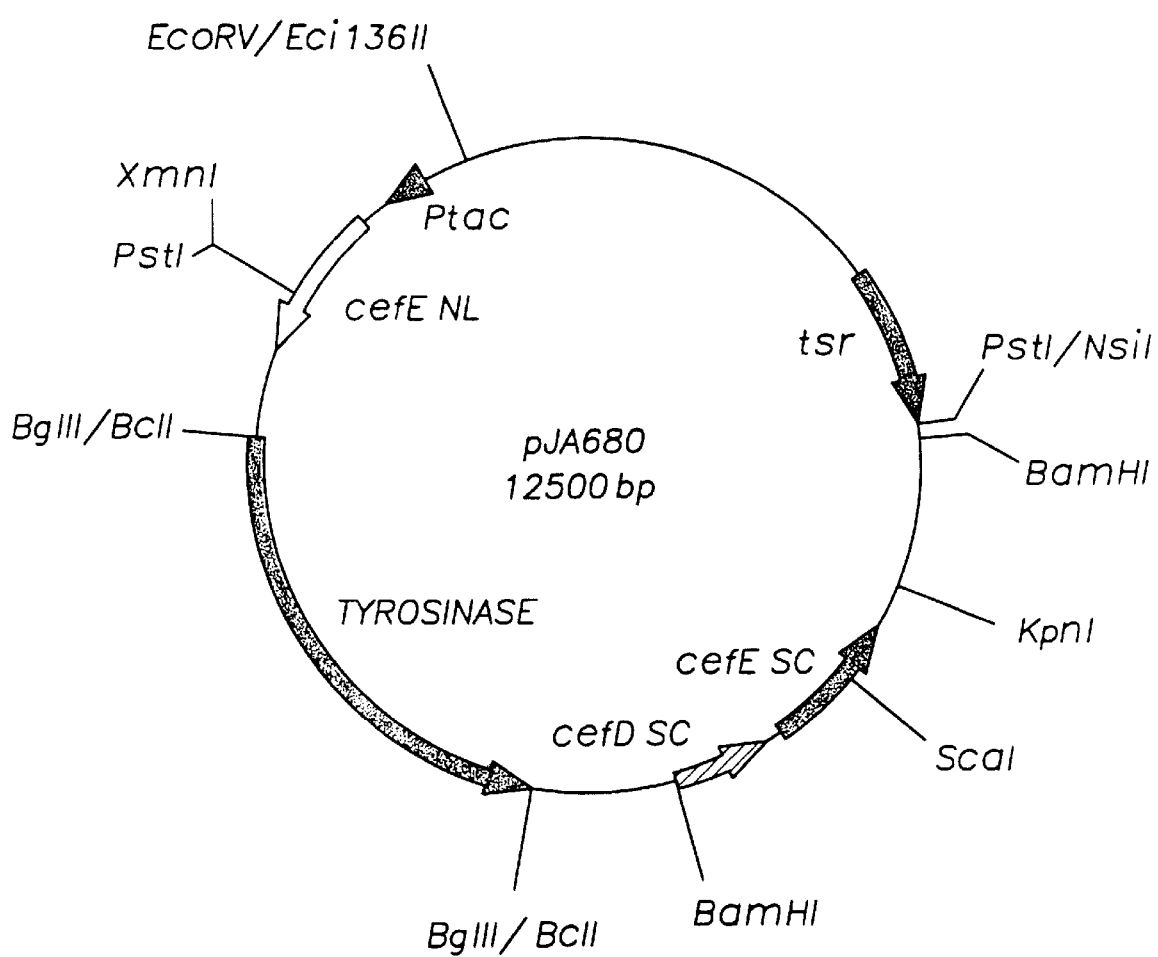
Figure 22A:
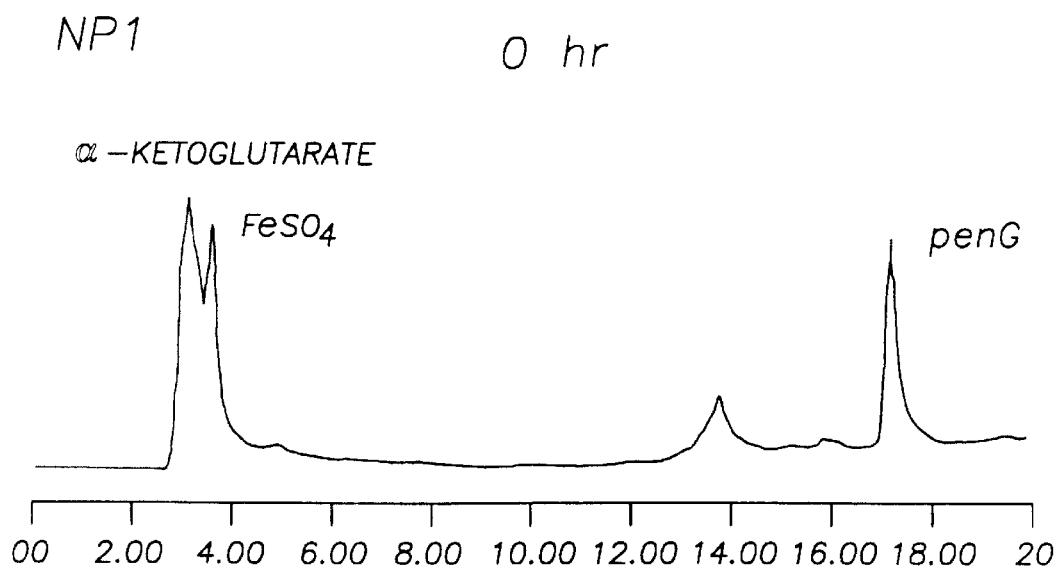
FIG. 22 shows HPLC profiles of ring expansion reactions.
Figure 22B:
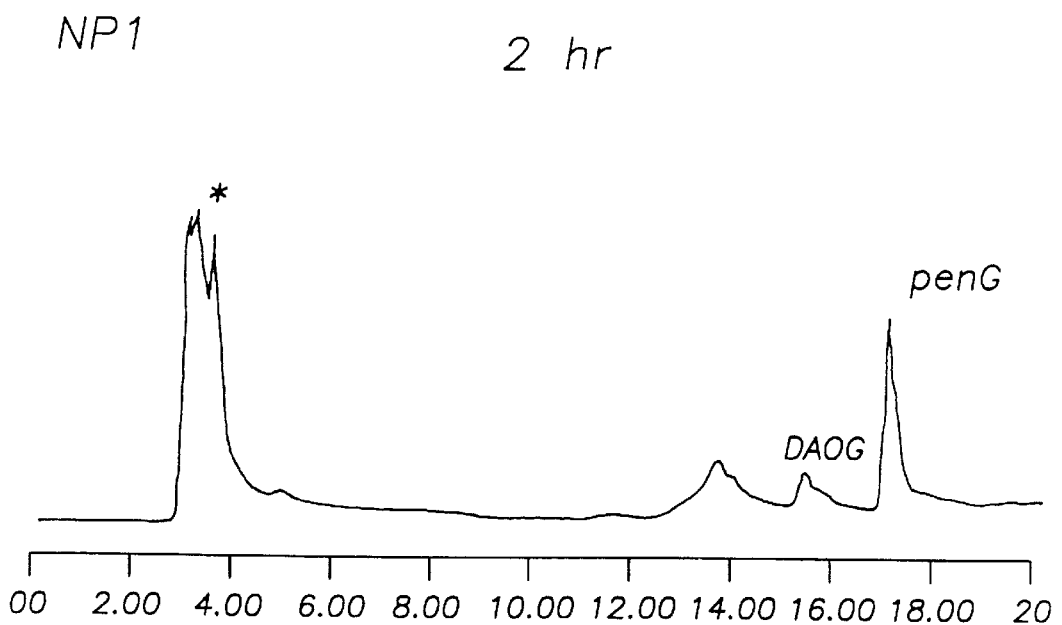
Figure 22C:
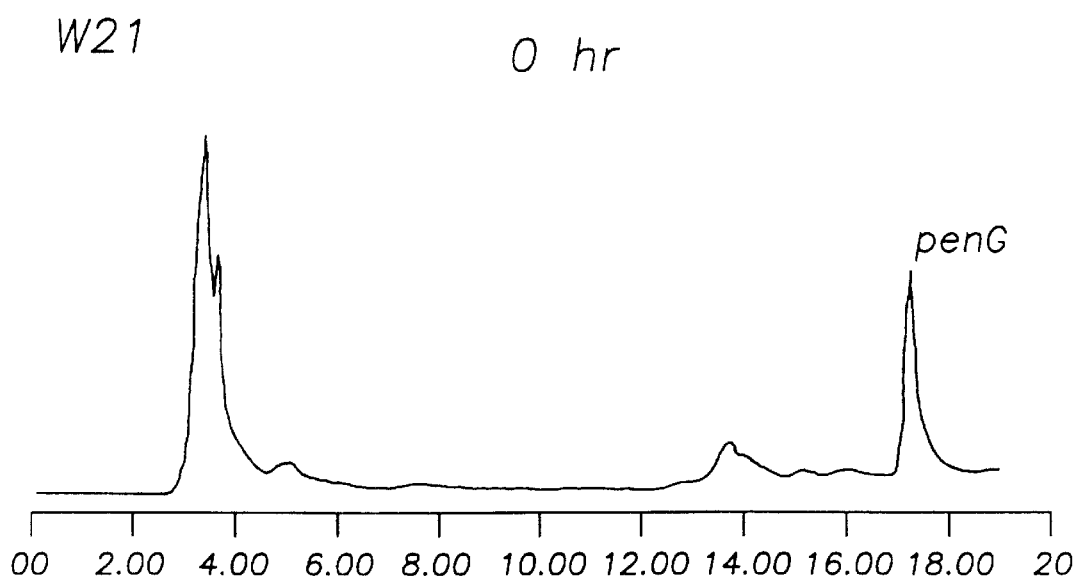
Figure 22D:
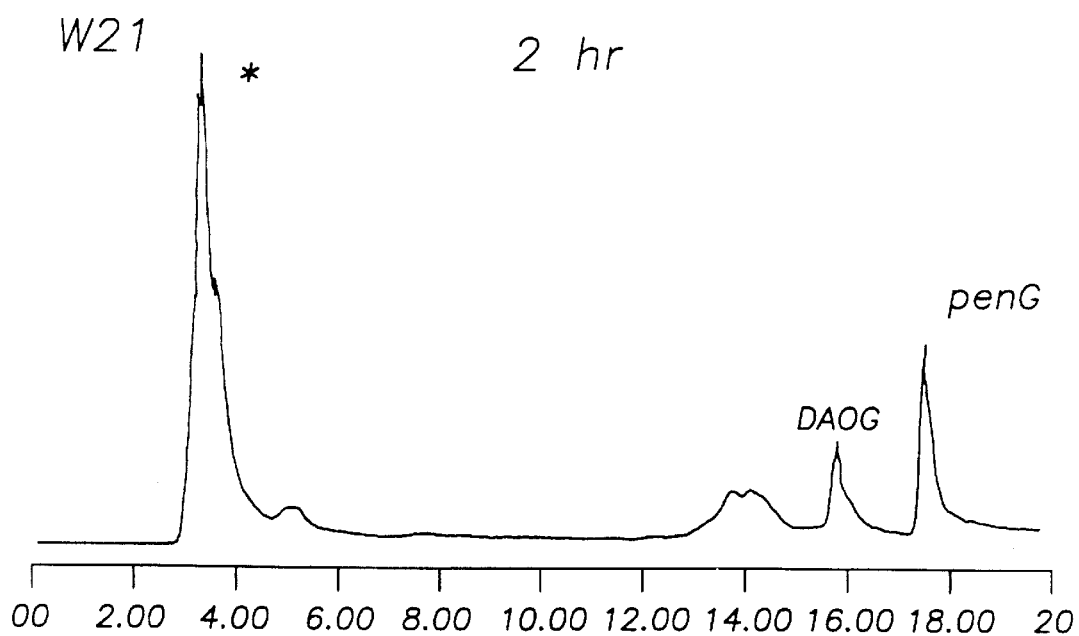
Figure 22E:
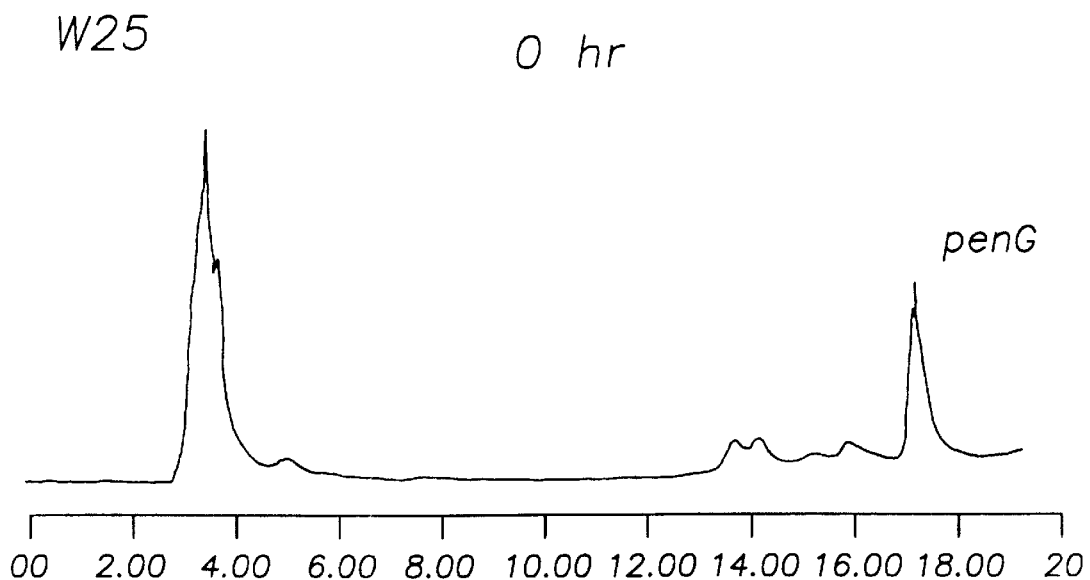
Figure 22F:
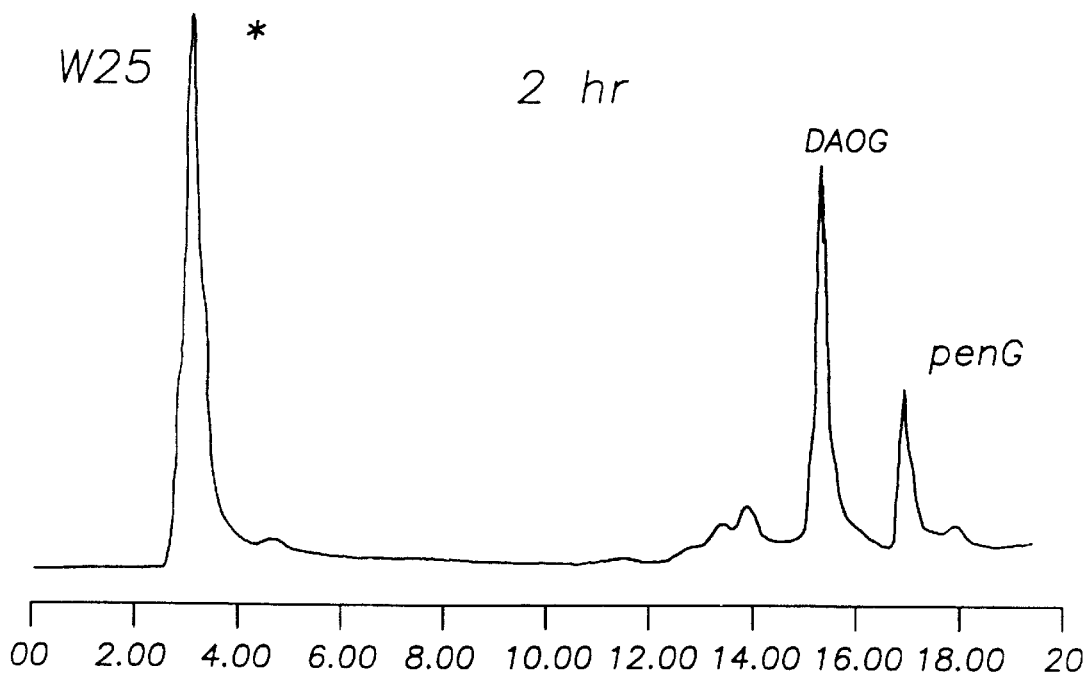
Figure 22G:
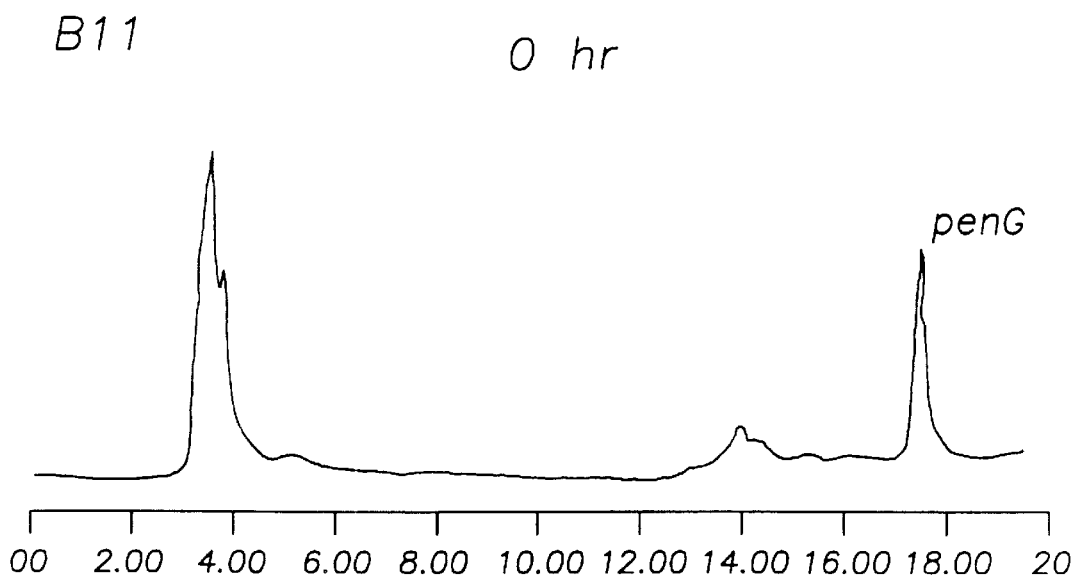
Figure 22H:
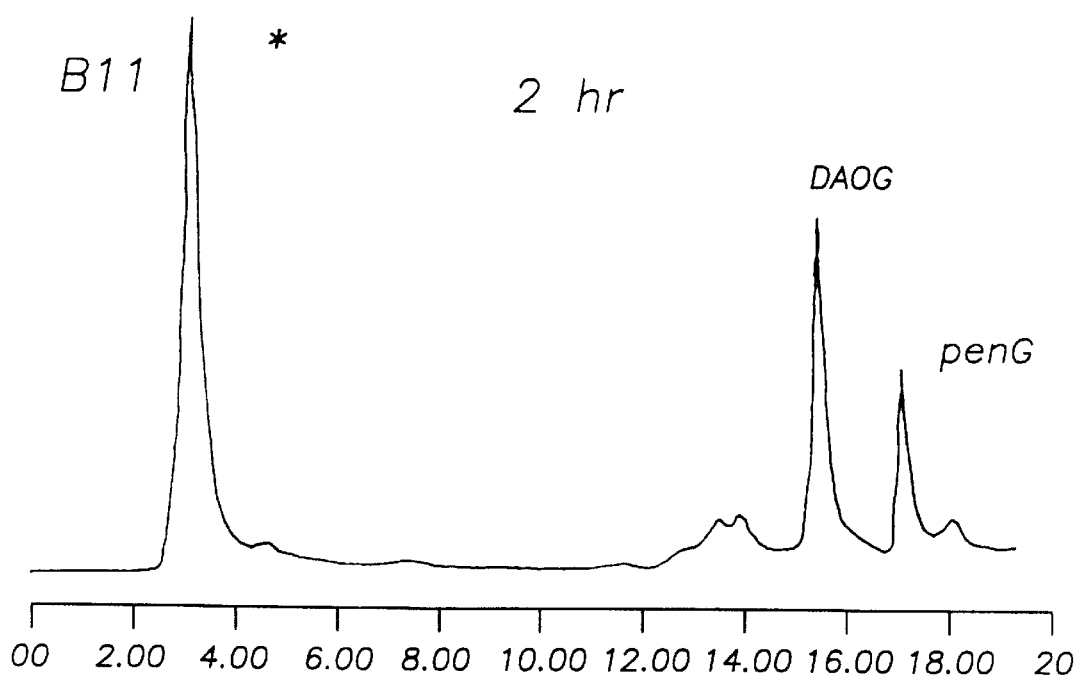

In the reactions depicted in FIGS. 18 and 19, both free and immobilized cells lost a considerable amount of their activity two hours. However, we found that the cells were able to re-initiate expandase reactions after being centrifuged (3500×g for 5 min at 4° C.) and washed in 0.05 M MOPS, pH 6.5 (FIG. 20). Interestingly, the free cells lost 60% of their activity after a single wash cycle and were completely inactivated after two cycles. Immobilized cells, by contrast, retained a good portion of their activity through at least four cycles.

We tested the activity of cells immobilized in other polymeric matrices, specifically agarose (4% w/v) and k-carrageenan (3% w/v), but did not observe cephalosporin production in either case, possibly due to cell and/or enzyme injury during immobilization.

Although the entrapped cells described here exhibited lower oxidative ring expansion activity than free resting cells, their immobilization may offer storage stability, recyclability, and operational stability for biotransformation of penicillins into cephalosporins.

Example 6

Construction of Hybrid Expandases Through Gene Shuffling by Homologous Recombination Materials and Methods Strains, Media and Culture Conditions: *Escherichia coli* DH5α (Gibco BRL, Gaithersburg, Md.) and ER1447 (New England Biolabs, Beverly, Mass.; Palmer et al., *Gene* 143:1–12, 1994) were used as host strains for transformations and recombination experiments. The *E. coli* ESS mutant described above was used as the indicator in the bioassay. Both *E. coli* strains were grown in LB (1% Tryptone, 0.5% NaCl, 0.5% Yeast Extract, 0.1% glucose) at 37° C.

*Streptomyces lividans* 1326 was grown on CG medium (0.4% Yeast Extract, 1% Malt Extract, 0.4% glucose; adjusted to pH 7.3 with KOH) or R2YE (Hopwood et al., *Meth. Enzymol.* 153:116–167, 1987) at 30° C.

For ring expansion activity, cells were grown in MST (1% soluble starch, 3% Trypticase Soy Broth without Dextrose [BBL, Cockeysville, Md.], 90 mM MOPS; pH adjusted to 7.0 with KOH before autoclaving.

DNA Manipulation and Transformation: Plasmid isolation and transformation into *E. coli* were carried out using standard protocols (Sambrook et al., *Molecular Cloning: A Laboratory Manual,* Cold Spring Harbor Laboratory Press, Cold Spring Harbor, N.Y., 1989). Protoplast preparation and transformation of Streptomyces were performed following the methods described by Hopwood et al.(Hopwood et al., *Manipulation of Streptomyces: a Laboratory Manual,* Norwich: John Innes Foundation, 1985). For restriction enzyme digestions, the DNA was purified using QIAprep Spin Miniprep Kit or QIAGEN plasmid Kit (QIAgen Inc., Valencia, Calif.). Restriction enzyme digestions and ligations were carried out as recommended by the manufacturers (Boehringer Mannheim and New England Biolabs).

Plasmid Constructions (see FIG. 21):pJALC: A 3 kb BamHI fragment from pULFJ32 (J. F. Martin, University of León, Spain) containing the cefE gene (and part of the cefD gene) from *S. clavuligerus* NRRL3585 was cloned into pCYB160 (derived from pCYB1, New England Biolabs), which already contained the cefE gene from *N. lactamdurans*.

pJALTC: A 2.3 kb KpnI fragment from pMEA4 (Hintermann, *Aspects of the Genomic Organisation in Streptomyces glaucescens,* Ph.D. dissertation, ETH, Zurich, 1984) containing the tyrosinase gene from *S. glaucescens* was cloned into pSP73 (Promega, Madison, Wis.) to yield pJA73T-SP6. A 2.3 kb EcoRI-HindIII fragment from this plasmid was then ligated with pIJ487 (Hopwood et al., *Meth. Enzymol.* 153:116–167, 1987) to yield plasmid pJA487T. This plasmid was then digested with BclI and the largest fragment (about 3 kb) was extracted from the agarose gel using GeneCleanII (Bio101, Vista, Calif.) and ligated into the BglII site of pJALC to give pJALTC.

pJA680: pJALTC was digested with EcoRV and NsiI and the 8.6 kb fragment, containing both cefE genes and the tyrosinase gene, was extracted as mentioned above and inserted into the PstI-Ecl136II digested Streptomyces vector pIJ680 to create pJA680.

Recombination in *E. Coli*: *E. coli* ER1447 (a recA$^+$ strain) was transformed with pJALC and, after heat shock, the cells were incubated overnight in 5 ml of LB containing ampicillin (100 μg/ml). Every 10–12 h, a 100 μl sample was transferred to a tube containing new medium (up to four rounds of growth). Samples of 1 ml were taken from each tube and plasmid DNA was isolated, digested with BglII and dephosporylated with CIP (Boehringer Mannheim, Germany). These DNA preparations were used to transform *E. coli* DH5α.

Recombination in *S. Lividans* Cells: Protoplats of *S. lividans* 1326 were transformed with pJA680 and plated on R2YE containing thiostrepton (50 μg/ml). Transformants were incubated at 30° C. for 5–7 days to allow sporulation. Spore suspension was prepared according to Hopwood et al. (Hopwood et al., *Genetic Manipulation of Streptomyces: a Laboratory Manual,* Norwich: John Innes Foundation, 1985) and aliquots were stored in 20% glycerol at −80° C. Dilutions from this suspension were then spread on CG medium supplemented with: 50 μg/ml thiostrepton, 0.3 g/l L-tyrosine, 0.1 g/l L-methionine, 0.5 g/l L-leucine, and 5 mg/l $CuSO_4$. Plates were incubated at 30° C. for 7 days.

Preparation of Cell-free Extracts from *S. Lividans* Cells: For each recombinant, a 250 ml baffled flask containing 50 ml of MST+thiostrepton (5 μg/ml) was inoculated with 5 ml from a seed culture previously grown in the same medium for 72 h. Cells were then incubated at 30° C., 200 rpm for 48 h. To prepare the extracts, cells were harvested by centrifugation (10,000×g, 10 min, 4° C.) and washed twice with 50 mM Tris.HCl pH 7.4 containing 0.1 mM DTT. The pellet was resuspended in 5 ml of the same buffer and cells were disrupted by four 25-sec sonication treatments (setting 5; 50% duty cycle) using a Branson Sonifier (Branson Sonic Power Co, Danbury, Conn.). Cell debris was removed by centrifugation (14,000×g, 30 min, 4° C.). Protein concentration was measured using the Bio-Rad protein assay (Bio-Rad, Hercules, Calif.). Bovine serum albumine was used as standard.

Ring Expansion Reaction: Ring expansion activity was measured in reactions mixtures containing 4 mM ascorbic acid, 8 mM $MgSO_4$, 8 mM KCl, 1.8 mM $FeSO_4$, 1.28 mM α-ketoglutarate, 4 mg protein/ml, and 50 mM Tris Tris.HCl pH 7.4 in a final volume of 2.5 ml. Penicillin G was used as substrate at a final concentration of 5.6 mM. The ring expansion was conducted in test tubes incubated at 30° C., 200 rpm for 2 h. Samples of 0.5 ml were taken and reaction was stopped by adding the same volume of methanol.

Bioassay of Product: Cephalosporins were assayed by the agar plate diffusion method described above. Paper discs saturated with 20 μl from the reaction mixtures were placed on LB agar (0.8% agar) medium seeded with *E. coli* ESS. The medium also contained 50,000 IU/ml of penicillinase (Bacto Penase Concentrate, Difco, Detroit, Mich.) which destroys the substrate penicillin G, but not cephalosporins. The plates were incubated overnight at 37° C.

HPLC Analysis: Methanol-treated samples (20 μl) were analyzed using a Waters Module I with a 486M1 detector, W600 pump and μBondapack C18 column (300×3.9 mm) (Waters Associate, Milford, Mass.). The flow rate was 1 ml/min with detection at 260 nm. The elution was done using 10 mM $KH_2PO_4$ (adjusted to pH 3 with concentrated $H_3PO_4$)-methanol (80:20 v/v) in the isocratic mode during the first 5 min. followed by a 15 min linear gradient from 100% of the initial solvent ($KH_2PO_4$-methanol) to 100% methanol.

DNA Sequencing: To sequence the hybrid cefE genes, we used two different oligonucleotides depending on where recombination was located. For those *E. coli* clones containing both PstI sites (see Results) we used a 22 bp primer (5'-CCACCAGACCCCTTGCGCGAAC-3') located 16 bp upstream the PstI site on the cefE of *N. lactamdurans* (FIG. 20). For *E. coli* clones containing only one PstI side and those obtained in *S. lividans,* we used a 22 bp primer (5'-GAGCGGATAACAATTTCACACA-3') located within the Ptac promoter (FIG. 20).

Results

Recombination in *E. Coli*: We first generated hybrid expandase genes by homologous recombination in *E. coli.* Specifically, we produced a bacterial plasmid, pJALC, containing the *S. clavuligerus* and *N. lactamdurans* expandase genes in tandem. The plasmid was constructed so that a BglII site was situated between the two genes and could be used as a diagnostic to determine whether or not recombination between the genes had occurred.

The plasmid was transformed into recA+ E. coli and the cells were grown up in order to allow recombination to occur. Plasmids were isolated back out of the cells and digested with BglII so that plasmids that had not undergone recombination were linearized, and the digested population was then transformed into DH5α cells. Sixty-three DH5α colonies were analyzed to determine whether recombination had occurred, as expected. Seventeen of those colonies were found to contain an approximately 8 kb plasmid, the expected size for a plasmid that had undergone recombination between the two expandase genes.

Plasmids were isolated from the seventeen colonies, and were subjected to restriction analysis (see Table 6). Five of the plasmids gave two bands after digestion with PstI, indicating that recombination had occurred at a site after the PstI site in the *N. lactamdurans* expandase gene. The remaining plasmids each gave a single band when digested with PstI, indicating that one of the two PstI sites originally present in pJALC had disappeared. Further digestion and sequencing analysis indicated that the PstI site in the *N. lactamdurans* expandase was no longer present in these plasmids.

TABLE 6

Restriction analysis of different clones (containing a 8 kb plasmid) obtained after transformation of *E. coli* DH5α.

| plasmid | undigested | + BglII | + BamHI | + PstI |
|---|---|---|---|---|
| pJALC | 11 | 11 | 8, 3* | 6, 5 |
| pJAR2-4 | 8 | nd** | 8 | 8 |
| pJAR3-4 | 8 | nd | 8 | 8 |
| pJAR4-9 | 8 | nd | 8 | 8 |
| pJAR3-8 | 8 | nd | 8 | 6.1, 1.9 |
| pJAR4-52 | 8 | nd | 8 | 6.1, 1.9 |

The nucleotide sequences at the recombination junctions were determined for the plasmids isolated from DH5α (see FIG. 22). As shown, recombination occurred after stretches of identical sequence in the range of 2–21 bp long.

Recombination in *S. Lividans*: We also generated hybrid expandase genes by recombination in Streptomyces. In this case, we produced a plasmid, pJA680, containing the *S. clavuligerus* and *N. lactamdurans* expandase genes in tandem, separated by the *Streptomyces glaucescens* tyrosinase gene. When tyrosinase is active, it produces the melanin pigment, which diffuses into the agar as a black splotch. Recombination between the expandase genes is expected to delete the tyrosinase gene from the plasmid, so that colonies containing recombinant plasmids can be identified by the absence of melanin production.

The plasmid was introduced into *Streptomyces lividans* cells and white colonies were identified. Plasmids were prepared from both white and black colonies. All black colonies contained plasmids that were 12.5 kb in size, the size of intact pJA680; none appeared to contain recombinant plasmids, which were expected to be approximately 6.3 kb in size. Of 58 white colonies that were analyzed, 37 (63.7%) contained a 6.3 kb plasmid, 17 (19.3%) contained a 5.8 kb plasmid, 2 (3.45%) contained an 8 kb plasmid, and 2 (2.45%) contained a 4 kb plasmid.

Restriction analysis of plasmids isolated from two strains (W21 and W64) containing a 6.3 kb plasmid, two strains (W25 and W76) containing an 8 kb plasmid, and one strain (B18) containing pJA680, showed that plasmids from W21 and W64 were not cleaved by PstI or XmnI; plasmids from W25 and W76 were cut by XmnI, BamHI, and ScaI, but not by PstI. From these data, we concluded that W21 and W64 were both missing at least part of the *N. lactamdurans* expandase gene; W25 and W76 were also missing part of the *N. lactamdurans* gene but appeared to have an intact *S. clavuligerus* gene.

We tested the putative recombinant plasmids that we had isolated by assaying the ring expansion activity of the enzymes they encoded (see Table 7). We found that none of the strains containing plasmids 4 kb or 5.8 kb in size produced zones of growth inhibition in our bioassay. One strain, W21, containing a 6.3 kb plasmid produced a clear zone, as did both of the strains (W25 and W76) containing 8 kb plasmids.

TABLE 7

Ring Expansion Activity of Strains Containing Hybrid Plasmids

| plasmid size (kb) | strain | clear zone |
|---|---|---|
| 4 | W3 | − |
| " | W53 | − |
| 5.8 | W6 | − |
| " | W20 | − |
| " | W23 | − |
| " | W39 | − |
| " | W45 | − |
| 6.3 | W4 | − |
| " | W5 | − |
| " | W21 | + |
| " | W26 | − |
| " | W32 | − |
| " | W33 | − |
| " | W34 | − |
| " | W36 | − |
| " | W41 | − |
| " | W48 | − |
| " | W49 | − |
| " | W55 | − |
| " | W61 | − |
| " | W62 | − |
| " | W64 | − |
| " | W69 | − |
| " | W72 | − |
| " | W77 | − |
| 8 | W25 | + |
| " | W76 | + |
| 12.5 | B11 | + |
| " | B18 | + |

To confirm that the clear zones we were observing in our growth inhibition assay resulted from the production of DAOG, we analyzed all positive samples by HPLC. As shown in FIG. 22, the 0 h samples gave a profile showing several peaks corresponding to α-ketoglutarate (3.1 min), $FeSO_4$ (3.6 min), and penicillin G (17.2 min). After 2 h of incubation, the peak corresponding to DAOG (15.5 min) was clearly present on the chromatograms, as was another unidentified peak eluting at 3.35 min.

FIG. 21 gives the sequences of the crossover junctions present in hybrid expandase genes isolated from *E. coli*. Numbers at both sides of the sequences indicate the position (bp) within the genes. Underlined letters indicate identical sequences. Clones shown in Panel (A) contain two PstI sites. pJAR4–8 and pJAR4–52 showed the crossover junctions at the same position as pJAR3–8, whereas pJAR4–6 was similar to pJAR4–5. Clones shown in Panel (B) contain only one PstI site. pJAR3–7 and pJAR3–9 showed crossover junctions at the same location as pJAR4–9.

Example 7

Expansion of Penicillin G and Ampicillin by Recombinant Strains of *S. lividans*

Materials and Methods

Microorganism, Medium and Culture Conditions: *S. lividans* 1326 was used in all experiments. Cultures were grown in 250 ml baffled flasks containing 40 ml of MST medium. Each flask was inoculated with 50 µl of a spore suspension (prepared and stored at −80° C. in 20% glycerol) and incubated at 30° C., 250 rpm, for 48 h.

Transformation: Protoplasts preparation and transformation were done following the protocols described previously (Hopwood et al., *Meth. Enzymol.* 153:116–167, 1987).

Plasmids: The plasmid pUL702-202a was a gift from J. F. Martin (University of León, Spain). This vector harboured a 4.3 Kb BglII fragment containing the epimerase and expandase genes from *Nocardia lactamdurans* inserted at the BglII site on pIJ702. The plasmid pHJ11 was constructed by cloning a 3 Kb BglII fragment containing the expandase gene from *S. clavuligerus* 3585 into pIJ702 at the BglII site.

Ring Expansion Reaction: The ring expansion mixture contained 1.8 mM FeSO$_4$, 1.28 mM α-ketoglutarate, 6 mg/ml protein (cell-free extract), 8 mM KCl, 8 mM MgSO$_4$, 14 mM DTT and 50 mM TrisHCl (pH 7.4) in a final volume of 2.5 ml. Substrate concentration was 5.6 mM. Additions were made following the order established by Shen et al. (*Enzyme Microb. Technol.* 6:402–404, 1984). Reaction mixtures were incubated in test tubes at 220 rpm, 30° C. At different times, 0.5 ml samples were taken and the reaction was stopped by adding 0.5 ml of methanol. Samples were centrifuged and supernatants were transferred to new tubes. Biotransformation activity was detected by paper disc-agar diffusion bioassay.

Bioassay of Product: Paper discs were saturated with 200 µl of supernatant. Two discs were superimposed and 4×50 µl of sample were applied. After each application, the discs were allowed to dry for 30 min under a laminar hood and, finally, they were placed on LB 0.8% agar medium seeded with *E. coli* ESS, and the plates were incubated overnight at 37° C.

Results

When the reaction was carried out using cell-free extracts of *S. lividans* containing the plasmid pUL702-202a (expandase from *N. lactamdurans*), expansion was only observed when penicillin G was used as substrate. After 2 h of reaction, production of cephalosporins was approximately 8 µg/ml. On the other hand, the strain pHJ11 (a transformant containing the expandase from *S. clavuligerus*) was able to expand both penicillin G and ampicillin. After 4 h of reaction and using penicillin G as substrate, production of cephalosporins was about 7 µg/ml; cephalosporin production was about 1.5 µg/ml when ampicillin was used as a substrate.

Other Embodiments

Those of ordinary skill in the art will recognize that the foregoing has been a description only of certain preferred embodiments of the present invention, which description is not intended to limit the invention's scope. It will be apparent that various alterations and substitutions can readily be made without departing from the spirit or scope of the invention, as that is defined in the following claims. To give but one example, those of ordinary skill in the art will appreciate that the system described herein can also be used for the production of cephamycins so long as cephalosporin precursors produced by ring expansion from penicillins can be modified by methoxylating enzymes.

What is claimed is:

1. A method of converting a penicillin other than penicillin N or ampicillin to a cephalosporin, the method comprising steps of:
providing a source of naturally occurring expandase enzyme, which expandase enzyme is not produced in a cell that also naturally produces the penicillin substrate;
providing exogenously a penicillin substrate other than penicillin N, ampicillin, or a penicillin having the formula:

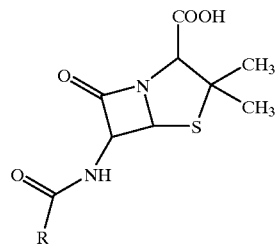

wherein R is 3-carboxybenzyl or a hydrocarbon containing 1–4 carbon atoms terminally substituted with a radical selected from the group consisting of carboxy, amino, and combinations thereof;
contacting the expandase with the penicillin substrate under conditions that allow the expandase to expand the penicillin substrate.

2. The method of claim 1 wherein the step of providing a source of expandase comprises providing resting cells, growing cells, or immobilized cells that have produced expandase.

3. The method of claim 2 wherein the cells are cells that naturally express the expandase.

4. The method of claim 3 wherein the cells are selected from the group consisting of *Xanthomonas lactamgena*, *Lysobacter lactamgenus*, *Flavobacterium sp.*, *Flavobacterium chitinovorum*, *Streptomyces organanensis*, *Nocardia lactamdurans*, *Streptomyces lipmanii*, *Streptomyces jumonjinensis*, *Streptomyces wadayamensis*, *Streptomyces cattleya*, *Streptomyces lactamgens*, *Streptomyces fradiae*, *Streptomyces griseus*, *Streptomyces olivaceus*, *Streptomyces sp.*, and *Cephalosporum acremonium* cells.

5. The method of claim 2 wherein the step of providing a source of expandase enzyme comprises providing cells that produce *S. clavuligerus* expandase.

6. The method of claim 2 wherein the step of providing a source of expandase comprises providing cells that express an expandase gene that is foreign to the cells.

7. The method of claim 6 wherein the expandase gene is selected from the group consisting of the *S clavuligerus* expandase gene and the *C. acremonium* expandase gene.

8. The method of claim 6 wherein the step of providing a source of expandase enzyme comprises providing *S. clavuligerus* cells.

9. The method of claim 6 wherein the step of providing a source of expandase enzyme comprises providing cells other than *S. clavuligerus* cells, which provided cells have been engineered to express the *S. clavuligerus* expandase gene.

10. The method of claim 1 wherein the step of providing a source of expandase comprises providing extract of a cell that produces expandase.

11. The method of claim 1 wherein the step of providing a source of expandase comprises providing purified expandase.

12. The method of claim 11 wherein the step of providing a source of expandase comprises providing pure expandase.

13. The method of claim 11 wherein the step of providing a source of expandase comprises providing an immobilized pure enzyme.

14. The method of claim 1 wherein the step of providing a source of expandase enzyme comprises providing a source of an enzyme selected from the group consisting of *S. clavuligerus* expandase and *C. acremonium* expandase.

15. The method of claim 1 wherein the step of providing a penicillin substrate comprises providing a substrate selected from the group consisting of: amoxicillin, butyryl-6-APA, decanoyl-6-APA, heptanoyl-6-APA, hexanoyl-6-APA, nonanoyl-6-APA, octanoyl-6-APA, penicillin F, penicillin G, penicillin V, penicillin mX, penicillin X, 2-thiophenylacetyl-6-APA, and valeryl-6-APA.

16. The method of claim 1 wherein the step of providing a penicillin substrate comprises providing a substrate selected from the group consisting of: penicillin V, penicillin G, penicillin mK, penicillin X, 2-thiophenylacetyl-6-APA, and amoxicillin.

17. The method of claim 1 wherein the penicillin substrate is different from whatever substrate the expandase expands in nature.

18. The method of claim 1 wherein the step of providing a penicillin substrate comprises providing a penicillin other than a penicillin naturally produced by the organism from which the provided expandase originated.

19. A method of converting a penicillin other than penicillin N to a cephalosporin, the method comprising the steps of:

providing a source of expandase enzyme;
  providing exogenously a penicillin substrate other than penicillin N, ampicillin, or a penicillin having the formula:

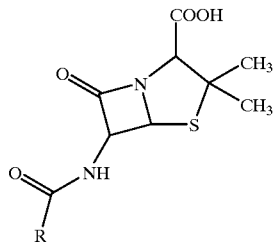

wherein R is 3-carboxybenzyl or a hydrocarbon containing 1–4 carbon atoms terminally substituted with a radical selected from the group consisting of carboxy, amino, and combinations thereof;

contacting the expandase with the penicillin substrate under conditions including:
    a ferrous ion ($Fe^{+2}$) concentration within the range of 0–4 mM;
    a concentration of α-ketoglutarate with the range of 0–4 mM; and
  isolating a cephalosporin.

20. A method of converting a penicillin other than penicillin N to a cephalosporin, the method comprising steps of:

providing a source of expandase enzyme, which expandase enzyme is substantially identical to that naturally found in *S. clavuligerus*;
  providing exogenously a penicillin substrate other than penicillin N, ampicillin, or a penicillin having the formula:

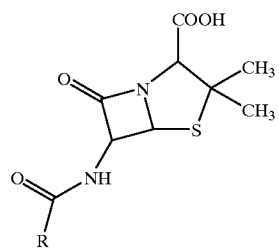

wherein R is 3-carboxybenzyl or a hydrocarbon containing 1–4 carbon atoms terminally substituted with a radical selected from the group consisting of carboxy, amino, and combinations thereof; and
  contacting the expandase with the penicillin substrate under conditions that allow the expandase to expand the penicillin substrate.

21. The method of claim 1, 19, or 20 wherein the penicillin substrate is penicillin G.

* * * * *